US012805849B2

United States Patent

(12) United States Patent
Jessop et al.

(10) Patent No.: US 12,805,849 B2
(45) Date of Patent: Nov. 24, 2026

(54) BREATH SAMPLING DEVICE

(71) Applicant: Owlstone Medical Limited, Cambridge (GB)

(72) Inventors: David Jessop, Cambridge (GB); Max Allsworth, Cambridge (GB)

(73) Assignee: Owlstone Medical Limited, Cambridge (GB)

( * ) Notice: Subject to any disclaimer, the term of this patent is extended or adjusted under 35 U.S.C. 154(b) by 306 days.

(21) Appl. No.: 18/580,913

(22) PCT Filed: Jul. 22, 2022

(86) PCT No.: PCT/GB2022/051927
§ 371 (c)(1),
(2) Date: Jan. 19, 2024

(87) PCT Pub. No.: WO2023/002215
PCT Pub. Date: Jan. 26, 2023

(65) Prior Publication Data
US 2025/0082309 A1 Mar. 13, 2025

(30) Foreign Application Priority Data
Jul. 22, 2021 (GB) ..................................... 2110582

(51) Int. Cl.
*A61B 5/00* (2006.01)
*A61B 10/00* (2006.01)

(52) U.S. Cl.
CPC ...... *A61B 10/00* (2013.01); *A61B 2010/0087* (2013.01)

(58) Field of Classification Search
CPC ........................ A61B 10/00; A61B 2010/0087
See application file for complete search history.

(56) References Cited

U.S. PATENT DOCUMENTS 9,643,186 B1 5/2017 Ahmad et al.
10,076,268 B1 * 9/2018 Dietrich ................ A61B 5/083
(Continued)

FOREIGN PATENT DOCUMENTS

CN 107145066 B 9/2020
CN 111671472 A * 9/2020 ............ A61B 10/00
(Continued)

OTHER PUBLICATIONS

European Patent Office, PCT International Search Report and Written Opinion, PCT/GB2022/051927, Sep. 29, 2022.
(Continued)

*Primary Examiner* — May A Abouelela
(74) *Attorney, Agent, or Firm* — Leveque Intellectual Property Law, P.C.

(57) ABSTRACT

The present techniques relate to sampling devices, and in particular to breath sampling devices. We describe a computer-implemented method of designing a breath sampling device comprising a housing through which a substantial portion of an exhaled breath passes and sorbent material which extends across a cross-section of the housing. The method comprises identifying a plurality of parameters of the device which are variable with different designs of the breath sampling device and selecting values of the plurality of parameters which maximise a global fitness value. The plurality of parameters comprises at least two of mass of the sorbent material, size of the sorbent material, thickness of the sorbent material, breakthrough volume and flowrate within the device.

21 Claims, 16 Drawing Sheets

(56) References Cited

U.S. PATENT DOCUMENTS

| | | | | |
|---|---|---|---|---|
| 10,258,276 | B2 * | 4/2019 | Abbott | A61B 5/486 |
| 11,426,097 | B1 * | 8/2022 | Lynn | F16K 31/52408 |
| 12,502,096 | B2 * | 12/2025 | Smith | A61B 5/082 |
| 2004/0162500 | A1 * | 8/2004 | Kline | A61B 10/0045 600/543 |
| 2007/0062255 | A1 | 3/2007 | Talton | |
| 2013/0006068 | A1 * | 1/2013 | Gemer | A61B 10/0051 600/314 |
| 2015/0038872 | A1 * | 2/2015 | Halter | A61B 5/0537 600/547 |
| 2015/0335267 | A1 * | 11/2015 | Cormier | A61B 5/0836 600/532 |
| 2016/0150995 | A1 * | 6/2016 | Ratto | A61B 5/4875 600/532 |
| 2017/0071580 | A1 * | 3/2017 | Artsyukhovich | A61B 5/097 |
| 2017/0119280 | A1 | 5/2017 | Ahmad et al. | |
| 2017/0188887 | A1 * | 7/2017 | Phillips | G01N 1/2202 |
| 2017/0303823 | A1 * | 10/2017 | Allsworth | A61M 16/06 |
| 2017/0304008 | A1 * | 10/2017 | Tam | G06T 7/73 |
| 2018/0328841 | A1 * | 11/2018 | Graham | A61B 5/0816 |
| 2018/0333101 | A1 * | 11/2018 | DeBates | A61B 5/097 |
| 2019/0015081 | A1 * | 1/2019 | Ssenyange | A61B 10/00 |
| 2019/0183418 | A1 * | 6/2019 | Hunt | A61B 5/412 |
| 2019/0269873 | A1 * | 9/2019 | Rodiera Olivé | A61M 16/01 |
| 2019/0274588 | A1 * | 9/2019 | Cardin | A61M 16/0057 |
| 2019/0307396 | A1 * | 10/2019 | Attariwala | G05D 16/06 |
| 2020/0015707 | A1 * | 1/2020 | Ratto | G01N 33/497 |
| 2020/0229799 | A1 * | 7/2020 | Ma | A61B 5/082 |
| 2020/0245898 | A1 * | 8/2020 | Heanue | A61B 10/00 |
| 2020/0245899 | A1 * | 8/2020 | Heanue | A61B 5/082 |
| 2020/0309753 | A1 * | 10/2020 | Mamerow | A61B 10/00 |
| 2021/0059560 | A1 * | 3/2021 | Allegra | A61B 10/00 |
| 2021/0113097 | A1 * | 4/2021 | Ohno | A61B 5/0205 |
| 2021/0177382 | A1 * | 6/2021 | Perdue | A61B 10/0045 |
| 2021/0186373 | A1 * | 6/2021 | Stumber | A61M 16/085 |
| 2021/0267478 | A1 * | 9/2021 | Purves | G01N 33/497 |
| 2021/0267482 | A1 * | 9/2021 | Purves | A61B 5/087 |
| 2021/0315483 | A1 * | 10/2021 | Laermer | A61B 10/0045 |
| 2021/0368880 | A1 * | 12/2021 | Kim | A41D 13/11 |
| 2022/0000420 | A1 * | 1/2022 | Rekow | A61B 5/082 |
| 2022/0031189 | A1 * | 2/2022 | de Jonge | A61B 5/097 |
| 2022/0317122 | A1 * | 10/2022 | Lapidot | G01N 33/56983 |
| 2022/0322963 | A1 * | 10/2022 | Bryden | A61B 5/082 |
| 2022/0354383 | A1 * | 11/2022 | Jia | A61B 5/087 |
| 2023/0157573 | A1 * | 5/2023 | Chen | A61B 5/097 600/532 |
| 2023/0210502 | A1 * | 7/2023 | Keane | A61B 5/097 435/287.2 |
| 2023/0293043 | A1 * | 9/2023 | Li | B01D 53/265 600/543 |
| 2023/0337935 | A1 * | 10/2023 | Smith | A61B 10/00 |
| 2024/0180444 | A1 * | 6/2024 | Hu | A61B 10/00 |

FOREIGN PATENT DOCUMENTS

| | | | | | |
|---|---|---|---|---|---|
| CN | 113009125 | A | * | 6/2021 | G01N 1/34 |
| EP | 4115802 | A1 | * | 1/2023 | A61B 5/097 |
| KR | 20220142695 | A | * | 10/2022 | A61B 10/00 |
| KR | 20220153946 | A | * | 11/2022 | C12Q 1/6844 |
| WO | 2017187120 | A1 | | 11/2017 | |
| WO | 2017187141 | A1 | | 11/2017 | |
| WO | WO-2022000850 | A1 | * | 1/2022 | A61B 10/00 |
| WO | WO-2022013413 | A1 | * | 1/2022 | G01N 33/575 |
| WO | WO-2022061550 | A1 | * | 3/2022 | A61B 10/00 |
| WO | WO-2022229280 | A1 | * | 11/2022 | A61B 5/097 |

OTHER PUBLICATIONS

Gao, Fuchang & Han, Lixing, "Implementing the Nelder-Mead simplex algorithm with adaptive parameters," Computational Optimization and Applications, 51, 259-277, May 2012. 10.1007/s10589-010-9329-3.

* cited by examiner

BREATH SAMPLING DEVICE

TECHNICAL FIELD

The present techniques relate to sampling devices, and in particular to breath sampling devices.

BACKGROUND

FIG. 1*a* shows ReCIVA® Breath Sampler which is a non-invasive breath sampling device 10 and which is described for example in patent publications WO2017/187120 or WO2017/187141. The breath sampling device 10 can collect volatile organic compound and respiratory droplet samples from exhaled breath. The breath sampling device 10 provides non-invasive sampling during normal tidal breathing with options for breath fraction targeting while ensuring patient safety and comfort. FIG. 1*b* shows the breath sampling device 10 in use by a subject.

FIG. 1*c* is a schematic drawing showing the operation of the breath sampling device 10. The device 10 comprises a plurality of sorbent tubes 12 which are used to sample the breath. Typically, each sorbent tube presents a pressure drop of approximately 24 mbar at a nominal flow rate of breath/air. Thus, as illustrated, only small amount of the exhaled breath (circa 2%) is typically sampled by each sorbent tube in the device. The amount is dependent on the breathing rate of the subject and the method of sampling the breath. Merely as an example, if a user breathes into the breath sampling device 10 with a rate of 10 L/min, approximately 0.8 L/min is sampled in the sorbent tubes 12 and 9.2 L/min passes through the device without being sampled. Furthermore, the sorbent tubes are arranged approximately perpendicularly to the direction that breath flows into the device from a user.

Given that only a small amount of the exhaled breath is captured in each breathing cycle, it is typically necessary to capture several breaths to ensure that a sufficient volume of exhaled breath has been sampled. The applicant has recognized the need for a breath sampling device that collects and samples more breath from the user/patient in each breathing cycle.

SUMMARY

According to the present techniques, there is provided a method and device as set forth in the appended claims. Other features of the invention will be apparent from the dependent claims, and the description which follows.

We describe a computer-implemented method of designing a breath sampling device comprising a housing through which a substantial portion of an exhaled breath passes and sorbent material which extends across a cross-section of the housing, the method comprises identifying a plurality of parameters of the device which are variable with different designs of the breath sampling device and selecting values of the plurality of parameters which maximise a global fitness value. The plurality of parameters comprises at least two of mass of the sorbent material, size of the sorbent material, thickness of the sorbent material, breakthrough volume and flowrate within the device. The global fitness value is determined by: calculating a fitness value for a specific value of each of the selected plurality of parameters, wherein the fitness value is indicative of whether a design having the specific parameter value is suitable; and combining the fitness values for each of the plurality of parameters. The method may comprise calculating fitness values for multiple parameter values of each of the identified plurality of parameters and combining the calculated fitness values for each of the plurality of parameters to obtain multiple global fitness values. A calculated fitness value may be selected for each of plurality of parameters which maximises the global fitness value and it will be appreciated that by selecting a fitness value, a parameter value which corresponds to the fitness value is thus selected. The parameter values of the plurality of parameters which have the selected calculated fitness value may then be output. The skilled person will appreciate that maximising a global fitness value may comprise calculating at least one value for each parameter.

As explained in more detail below, the maximisation of the global fitness allows the values of the parameters of the device to be balanced to achieve an optimal device. In other words, the device may be designed to be relatively easy to breathe through, have a relatively low amount of sorbent material and collect a relatively high amount of breath (and hence volatile organic compound (VOC) of interest in the breath) when compared to existing designs or designs having different parameter values.

The breakthrough volume may be defined as the retention volume of a specific compound or compounds by the sorbent material. In other words the retention volume may be the volume of a specific compound or compounds in an exhaled breath which is actually sampled by the sorbent material as the exhaled breath passes through the device. The breakthrough volume can also be defined as the retention volume of the sorbent for specific compound(s) under defined conditions, such as humid and/or other conditions which are typically found in breath. As explained above, a breath sampling device having multiple sorbent tubes is only able to sample a small amount of the exhaled breath. This is partly due to the fact that only a small amount, perhaps 10% of the exhaled breath, passes through the section of the device in which the multiple sorbent tubes are located. By contrast, in the described device, the sorbent material extends across the cross-section of the housing through which the substantial portion of the breath passes. Thus, the device is able to sample across the cross-section of a substantial portion of the breath. An exhaled breath may be fractionated, with the initial portion, e.g. first 100 ml, of an exhaled breath being discarded because it is typically not useful for analysis. The remaining portion of the exhaled breath, e.g. 400 ml or so, may be sampled and may be termed the target portion of the exhaled breadth. A substantial portion may be above 80%, 90% and may even be up to 100% of an exhaled breath or where breath is fractionated may be above 80%, 90% and may even be up to 100% of the target portion of an exhaled breath. This may mean that a significantly larger volume of each exhaled breath is sampled with each breath cycle. Accordingly, it may be possible that only a single breath is required to reach the breakthrough volume and ensure accurate test results. The device may be a single shot sampler but it is also possible to collect multiple breaths. Changing the geometry of the sorbent material is complicated because the breakthrough volume depends on both flowrate (airspeed) within the device, thickness of the sorbent material and the sorbent material itself.

Selecting the calculated fitness values and hence values of the plurality of parameters which maximise a global fitness value may comprise using an optimisation algorithm. For example, initial values for each of the plurality of parameters may be set; initial fitness values for each of the initial values of the plurality of parameters may be calculated; the initial fitness values may be combined to obtain an initial global fitness value; and the optimisation algorithm may then be run to iteratively adjust the initial values for each of the plurality of parameters and repeat the calculating and combining steps until the global fitness value is maximised. The initial values may be set using any appropriate technique, e.g. a Monte Carlo method. It will be appreciated that by using an optimisation algorithm fitness values are calculated for multiple parameters value, each of which is an iteration from the initial parameter value. Similarly, multiple global fitness values are obtained by repeating the combining step. In other words, running the optimisation algorithm effectively calculates fitness values for multiple parameter values of each of the identified plurality of parameters and combines the calculated fitness values for each of the plurality of parameters to obtain multiple global fitness values.

As an alternative to running an optimisation algorithm, selecting values of the plurality of parameters which maximise a global fitness value may comprise calculating fitness values for multiple values of each of the selected plurality of parameters; combining the calculated fitness values to obtain multiple global fitness values; and indexing the multiple global fitness values to obtain the maximised global fitness value. In other words, large numbers of designs with different values of the plurality of parameters may be simulated so that the fitness values for each of the parameters may be calculated and stored in a database so that the maximum global fitness value can be extracted from the data.

Calculating a fitness value for a specific value may comprise defining a fitness function for each of the selected plurality of parameters and using the defined fitness function to calculate the fitness value for the specific value of the parameter. The fitness function describes the variation in the fitness value as a function of the parameter. The fitness value may vary between 0 and 1, where 0 indicates a completely unacceptable design and 1 indicates a completely acceptable design. When any one of the fitness values is zero, the method of combining the fitness values may be such that the global fitness value is also zero. This ensures that an unsuitable design is not output from the process. One way of combining the fitness values is to calculate the geometric mean. A weighted product which gives greater weight to some parameters than others may also be used.

The fitness functions may be considered to represent criteria which help evaluate the fitness of the design and thus they may represent practical or mechanical constraints on the device. The fitness functions may be represented by one or more error functions. For example, the fitness value for each of the breakthrough volume and the thickness of the sorbent material may approach 0 below a first threshold and 1 above a second threshold. This indicates that the first threshold must be satisfied, e.g. a particular volume of breath must be collected and the sorbent material must be thick enough. The skilled person will appreciate that it is hard to design the sorbent material if the sorbent material is too thin and wide. Above the second threshold, there is no further gain. In practice, the first and second thresholds may be set as unacceptable and ideal thresholds which allow for a small margin of error around the extremes of 0 and 1 and reflect the fact that the fitness function approaches 0 or 1 but may not achieve 0 and/or 1 exactly except for values of ±infinity. Thus, merely as an example the ideal value of the total volume of breath to achieve breakthrough volume which provides a fitness value of 0.99 may be $x_{ideal}=63$. Similarly, the unacceptable value of the total volume of breath which does not achieve breakthrough volume which provides a fitness value of 0.01 may be $x_{unacceptable}=57$. It will be appreciated that defining different fitness functions and/or different ideal and acceptable values is likely to change the result of the design.

The fitness value for each of the size of the sorbent material and the mass of the sorbent material may approach 1 below a first threshold and 0 above a second threshold. This indicates that once the first threshold is exceeded, e.g. the device is too large in size, the fitness of the design decreases with a further increase in the parameter until the second threshold is met and the design is completely unacceptable. The concept of ideal and unacceptable values may also be used. Merely as an example the ideal value of size (diameter) which provides a fitness value of 0.99 may be $x_{ideal}=20$ mm and the unacceptable value of size (diameter) which provides a fitness value of 0.01 may be $x_{unacceptable}=30$ mm. Size may be defined as cross-sectional area or for a regular shaped sorbent material, e.g. a disk, size may be defined by the diameter. The fitness function for the sorbent mass may be more complicated but in general, the lower the mass of sorbent that is used, the higher the fitness value.

The fitness function may be a combination of error functions. For example, the first error function may have a fitness value approaching 0 below a first airflow threshold and a fitness value approaching 1 once a second airflow threshold is exceeded with a smooth curve between the two thresholds and in the second error function, the device has a fitness value approaching 1 below a third airflow threshold and a fitness value approaching 0 once a fourth airflow threshold is exceeded with a smooth curve between the third and fourth thresholds. The concept of ideal and unacceptable values may also be used when combining error functions. For example, a range of ideal values for airflow may be defined as being between 35 and 150 L/min and the ranges for unacceptable values for airflow are below 25 and above 200 L/min.

The values of the breakthrough volume and flowrate are at least in part determined by the geometry of the sorbent material. Accordingly, varying the mass, size and/or thickness of the sorbent material may impact the values of the breakthrough volume and flowrate. The flowrate may also be dependent on lung data for a patient using the device. Thus, before calculating the fitness value, the method may comprise evaluating the breakthrough volume and flowrate, for example using one or more of the specific values for the mass, size and/or thickness of the sorbent material and the lung data. Where there are multiple sets of lung data, e.g. for different types of patient, the method may comprise calculating a fitness value for each of the selected parameters for each set of lung data.

In other words, the breakthrough volume and flowrate may be evaluated (e.g. calculated) using empirically derived formulae and/or well-known accurate formulae. For example, the breakthrough volume may be calculated by multiplying an obtained value for the specific breakthrough volume for a compound or compounds of interest (breakthrough volume per unit mass of the sorbent) by the mass of the sorbent material. The breakthrough volume may also take account of the effect of humidity and temperature from exhaled breath if it is derived empirically from a suitable measurement with air at the same temperature and humidity as human breath (circa 35° C.; 60-80% relative humidity). For instance, humidity can be taken into account by calculating what percentage of the sorbent material will be effectively inactivated by the water in the breath, under a specific set of conditions, and hence what percentage of sorbent material is available to capture the compound of interest. This reduction in sorbent material available to capture the compound of interest manifests itself as a reduction in the breakthrough volume. This can be countered by altering other parameters, such as increasing the bed depth of the sorbent material. The specific breakthrough volume may be interpolated from measurements based for example interpolated from measurements of breakthrough volume relative to airspeed and/or measurements of breakthrough volume relative to sorbent thickness. In other words, the breakthrough volume may be considered to be an empirically derived value which is dependent on airspeed and/or sorbent thickness. The sorbent thickness is known for a given iteration but the airspeed needs to be obtained. For example, the airspeed may be calculated from the flow rate (dV/dt) using a standard formula. The flow rate may be determined from flow resistance through the sorbent material and lung data. The flow resistance through the sorbent material may be calculated from the sorbent geometry and the sorbent flow resistivity.

Other components within the device may have an impact on the values of the breakthrough volume and/or flowrate. For example, the device may further comprise an orifice plate having an orifice which restricts the flowrate through the device. Thus an orifice plate may be used as an alternative to (or in addition to) increasing the amount of sorbent material. Generally, we are trying to keep the amount of sorbent material to a minimum and thus the use of an orifice plate may be beneficial. The plurality of parameters may further comprise orifice diameter and the method may comprise selecting a value of the orifice diameter which maximises the global fitness when selecting the other values. The method may further comprise evaluating the specific value of the flowrate based on a specific value of the orifice diameter, for example using standard formulae which define the impact of the orifice geometry on flowrate.

We also describe a method of making a breath sampling device having the output selected values. In other words, we also describe a breath sampling device comprising a housing through which, in use, a substantial portion of a breath exhaled into the breath sample device passes and sorbent material which extends across a cross-section of the housing, wherein the breath sampling device is made as described above. A substantial portion of a breath may be above 80% of the breath or target portion of the breath when a fractionated portion of the breath is excluded. The sorbent material may extend over at least 50%, or even over at least 70% of the cross-section.

We also describe a breath sampling device comprising: an inlet through which exhaled breath is received in the device; a first outlet through exhaled breath exits the device; a housing connected between the inlet and the first outlet and through which, in use, a substantial portion of a breath exhaled by a user into the device passes and a sorbent material which extends across a cross-section of the housing.

It will be appreciated that different optimized parameters will be output for different inputs, e.g. different fitness curves and/or different lung data. Merely, as an example the method described above may output the optimized parameters having a sorbent thickness of 4.03 mm and a sorbent diameter of 17.2 mm for a disk shaped sorbent material. Thus, the sorbent material may have a thickness of approximately 4.03 mm and a surface or cross-sectional area of approximately 232 $mm^2$. In another iteration, the method described above may output optimized parameters having a sorbent thickness of 2.5 mm and a sorbent diameter of 21.9 mm (i.e. a surface area of approximately 377 $mm^2$). In another iteration, the method described above may output optimized parameters having a sorbent thickness of 3.12 mm and a sorbent diameter of 25.6 mm (i.e. a surface area of approximately 515 $mm^2$). In each of the examples, the sorbent material has a width (diameter) which is significantly larger than its thickness which contrasts with a standard sorbent tube, for example the width may be between approximately 4 to 9 times the thickness. In other words, the sorbent material is large (i.e. wide) and thin.

The sorbent material may be a single piece, e.g. a disk or other suitable shape. Alternatively, the sorbent material may be formed from a plurality of discrete portions, e.g. disks or other shapes such as rectangular portions, wherein the total size of the discrete portions sums to the desired size. The discrete portions may each be the same or a different size. For example, a disk of diameter 21.9 mm may be formed from five discrete portions each having a diameter of 9.8 mm. The discrete portions may be supported in a sorbent holder. For example, each discrete portion may be held within a separate channel in the sorbent holder.

The device may further comprise an indicator indicating a volume of total breath which has been sampled by the device. The indicator may be a colour changing strip which changes colour when the total volume (and thus desired breakthrough volume) has been reached or a bag which inflates to a taut shape when the total volume (and thus desired breakthrough volume) has been reached. Such indicators are mechanical or chemical and do not introduce any electronic components. Alternatively, electronic equivalents may be used, for example, a spirometer may be included to measure the volume of total breath. The device may further comprise an indicator indicating a length of time that breath has been sampled by the device. When a user has exhaled through the device for a certain time (e.g. 7 minutes), the desired breakthrough volume is likely to have been achieved.

The device may further comprise an orifice plate having an orifice which restricts flow through the device. The orifice plate may be placed between the sorbent material and the outlet. The orifice plate may be held in place by an orifice plate holder. The diameter and length of the orifice may be adjusted according to the design of the device.

The device may further comprise a bypass component. The bypass component is configured to fractionate a breath cycle from a user. In other words, the bypass component is configured to allow an initial portion of an exhaled breath to exit the device without being sampled by the sorbent material. Typically the initial part of a breath cycle does not contain any useful data and is best discarded. The bypass component may be a mechanical component, e.g. a balloon or bag which inflates to a fixed volume or a flow switch. Again, this avoids the need for electronic components. The device may comprise a second outlet for exhaled breath and the bypass portion may be configured so that an initial portion of an exhaled breath exits the device through the second outlet.

The device may further comprise a filter which is between the inlet and the sorbent material and which filters out bacteria, viruses or other undesirable elements in the breath. A mouthpiece may be fitted to the inlet to facilitate use by a user. It will be appreciated that any combination of the indicator, orifice plate, bypass component, filter, mouthpiece may be incorporated in the device. Adaptors may be used to facilitate connections between components so that a fully modular device may be achieved. Additionally, the device may be a fully modular device in which components are placed in different orders along the flow path depending on the particular use. For example, a filter may be placed after the sorbent housing if the filter is expected to absorb volatile organic compounds (VOCs).

As will be appreciated by one skilled in the art, the method described above may be embodied as a system, or computer program product. Accordingly, present techniques may take the form of an entirely hardware embodiment, an entirely software embodiment, or an embodiment combining software and hardware aspects.

Furthermore, the present techniques may take the form of a computer program product embodied in a computer readable medium having computer readable program code embodied thereon. The computer readable medium may be a computer readable signal medium or a computer readable storage medium. A computer readable medium may be, for example, but is not limited to, an electronic, magnetic, optical, electromagnetic, infrared, or semiconductor system, apparatus, or device, or any suitable combination of the foregoing.

Computer program code for carrying out operations of the present techniques may be written in any combination of one or more programming languages, including object-oriented programming languages and conventional procedural programming languages. Code components may be embodied as procedures, methods, or the like, and may comprise sub-components which may take the form of instructions or sequences of instructions at any of the levels of abstraction, from the direct machine instructions of a native instruction set to high-level compiled or interpreted language constructs.

Embodiments of the present techniques also provide a non-transitory data carrier carrying code which, when implemented on a processor, causes the processor to carry out any of the methods described herein.

The techniques further provide processor control code to implement the above-described methods, for example on a general-purpose computer system or on a digital signal processor (DSP). The techniques also provide a carrier carrying processor control code to, when running, implement any of the above methods, in particular on a non-transitory data carrier. The code may be provided on a carrier such as a disk, a microprocessor, CD- or DVD-ROM, programmed memory such as non-volatile memory (e.g. Flash) or read-only memory (firmware), or on a data carrier such as an optical or electrical signal carrier. Code (and/or data) to implement embodiments of the techniques described herein may comprise source, object, or executable code in a conventional programming language (interpreted or compiled) such as Python, C, or assembly code, code for setting up or controlling an ASIC (Application Specific Integrated Circuit) or FPGA (Field Programmable Gate Array), or code for a hardware description language such as Verilog® or VHDL (Very high-speed integrated circuit Hardware Description Language). As the skilled person will appreciate, such code and/or data may be distributed between a plurality of coupled components in communication with one another. The techniques may comprise a controller which includes a microprocessor, working memory and program memory coupled to one or more of the components of the system.

It will also be clear to one of skill in the art that all or part of a logical method according to embodiments of the present techniques may suitably be embodied in a logic apparatus comprising logic elements to perform the steps of the above-described methods, and that such logic elements may comprise components such as logic gates in, for example a programmable logic array or application-specific integrated circuit. Such a logic arrangement may further be embodied in enabling elements for temporarily or permanently establishing logic structures in such an array or circuit using, for example, a virtual hardware descriptor language, which may be stored and transmitted using fixed or transmittable carrier media.

In an embodiment, the method of the present techniques may be realised in the form of a data carrier having functional data thereon, said functional data comprising functional computer data structures to, when loaded into a computer system or network and operated upon thereby, enable said computer system to perform all the steps of the above-described method.

Although a few preferred embodiments of the present invention are shown and described, it will be appreciated by those skilled in the art that various changes and modifications might be made without departing from the scope of the invention, as defined in the appended claims.

BRIEF DESCRIPTION OF DRAWINGS

For a better understanding of the invention, and to show how embodiments of the same may be carried into effect, reference will now be made, by way of example only, to the accompanying diagrammatic drawings in which.

DETAILED DESCRIPTION

Broadly speaking, we describe a breath sampling device that is configured to sample a significant portion (perhaps the entirety) of an exhaled breath from a user/patient. This is achieved by using a sampling device comprising adsorbent material having a geometry adapted for optimal results as explained below. The optimised geometry is one in which the thickness of the material is significantly smaller than the width of the material. In use, a user exhales into the device (once or several times or even hundreds of times), via a mouthpiece, and the exhaled breath passes through the adsorbent material whereby a large portion of the exhaled breath can be sampled and the desired volatile organic compound(s) within the breath can be adsorbed by the adsorbent material. As an example, the desired volatile organic compound(s) may be D5-ethanol. The breath capture is termed unassisted because the user provides the necessary pressure to push the breath through the device. Therefore, beneficially, the breath sampling device is optimized so that a user can comfortably and easily breathe through the device, and the device can collect as much volatile organic compounds (VOCs) as possible while using a minimum amount of sorbent in a reasonably sized geometry.

The features which are the same or substantially similar retain the same reference numbers in the Figures and throughout the description. Therefore, a repeated description of such features is omitted.

Figure 2A:
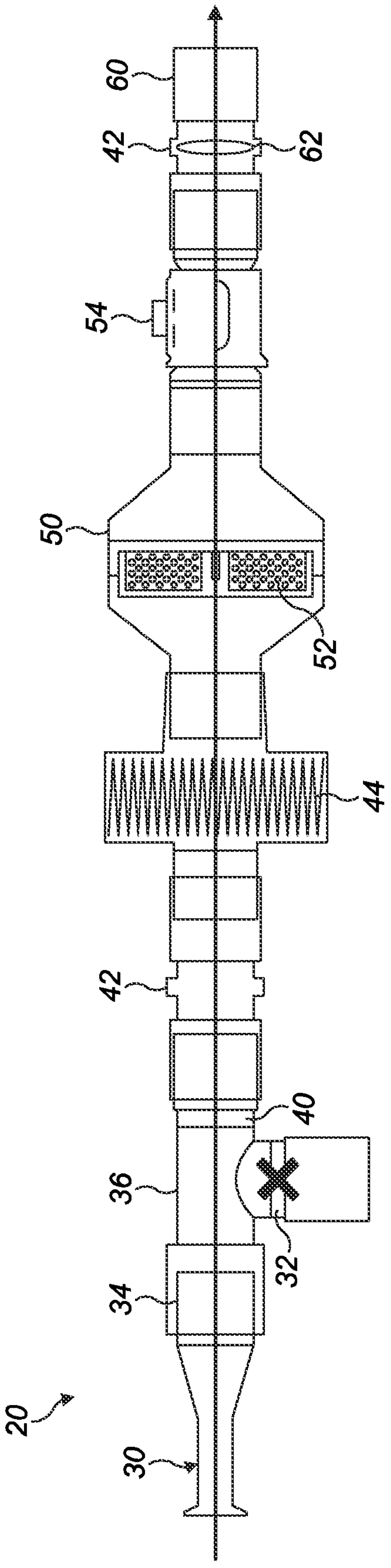
FIGS. 2*a* and 2*b* are cross-sectional views of a breath sampling device according to the techniques described in the present application showing the direction of flow of an exhaled breath and an inhaled breath through the device, respectively.
Figure 2B:
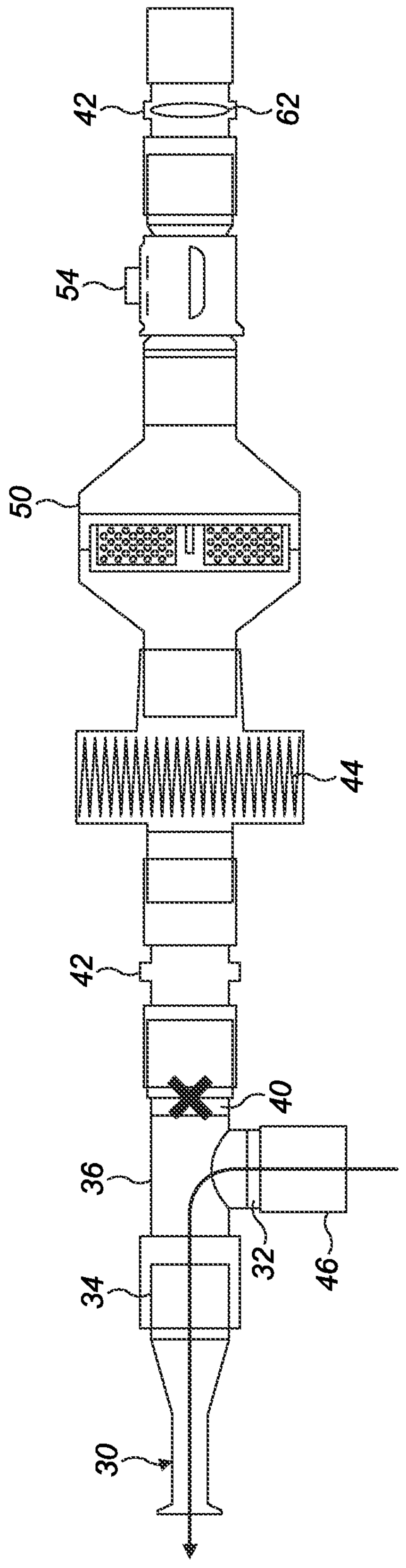

FIGS. 2*a* and 2*b* show a cross-section of one arrangement for a breath sampling device 20 according to the present techniques. In FIG. 2*a*, the direction of an exhaled breath through the device is shown using the arrow and similarly in FIG. 2*b*, the direction of an inhaled breath through the device is shown using the arrow. The breath sampling device 20 comprises an inlet 30 through which exhaled breath passes into the device, an outlet 60 for the exhaled breath and a housing 50 in which sorbent material 52 is located. The sorbent housing 50 is connected between the inlet 30 and the outlet 60 so that exhaled breath passes into the device 20, through the sorbent material 52 and out through the outlet 60. In this arrangement, the direction of flow of an exhaled breath through the sorbent material is approximately parallel to the direction of flow of a user's breath into the device through the inlet. As shown in FIG. 2*b*, the inlet 30 for exhaled breath also acts as the outlet 30 for inhaled breath. When inhaling, air is drawn through a second inlet 46 and passes straight to the outlet 30 via a one-way valve 32 which prevents air flow through the valve 32 when exhaling. There is also a second one-way valve 40 which prevents air flow through the valve 40 into the housing 50 when inhaling.

The sorbent material may also be termed an adsorbent material or sorbent, and the terms may be used interchangeably. The sorbent material 52 may be shaped as a disk or any suitable shape and the structure of the sorbent material 52 is described in more detail below. In particular, the sorbent material 52 extends across at least a substantial part (at least 50%), up to perhaps the entire, cross-section of the housing 50. In other words, the sorbent material 52 extends across the fluid path between the inlet and outlet whereby the sorbent material samples a substantial part of each exhaled breath, particularly a substantial part of a fractionated target breath. The sorbent material 52 may be made from activated carbon and/or zeolites and/or activated alumina and/or lignite coke and/or bentonite. A suitable material is carbosieve SIII 60-80 and/or Carboxen 569. Where appropriate, the sorbent material 52 may be baked, for instance at 250 degrees Celsius to condition the sorbent material to remove volatile compounds such as ethanol. The sorbent material 52 may be baked at even higher temperatures than 250 degrees Celsius, for example to recondition the sorbent by removing other volatile compounds.

Figure 1A:
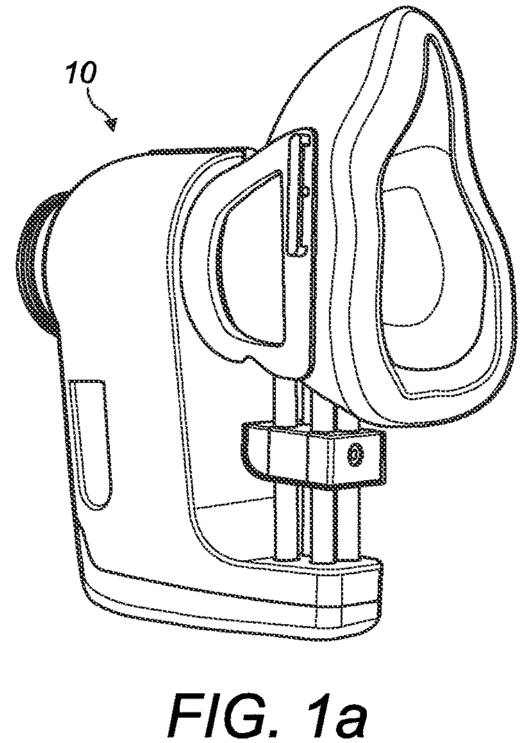
FIG. 1*a* is a breath sampling device known in the art.
Figure 1B:
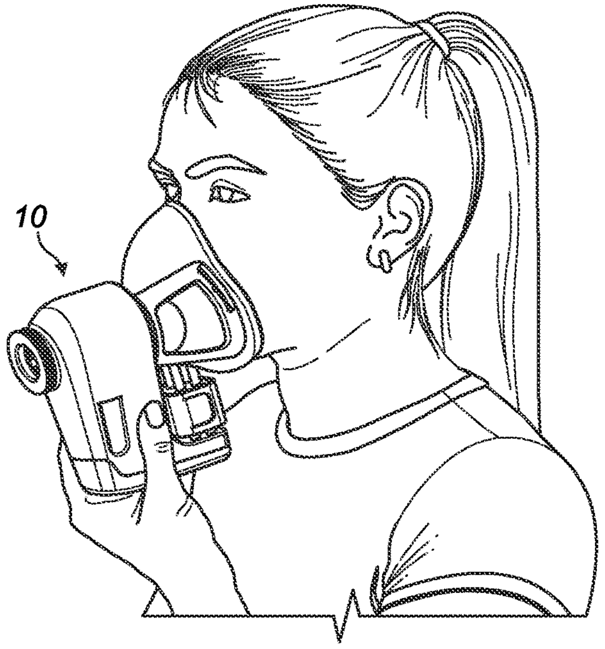
FIG. 1*b* is the breath sampling of FIG. 1*a* in use.
Figure 1C:
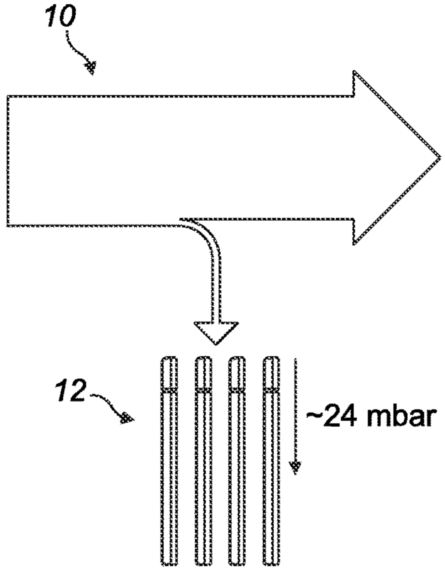
FIG. 1*c* is a schematic drawing of the breath sampling of FIG. 1*a;*

The inlet 30 through which exhaled breath passes into the device and which also acts as an outlet for inhaled breath to a user may be in the form of a mouthpiece. The mouthpiece is configured to be in connection with the one-way inlet valves 32, 40 to allow a user to keep the mouthpiece in their mouth when inhaling and exhaling. The mouthpiece ensures a non-invasive sampling during normal tidal breathing. In use, the user (who can be a patient), places the mouthpiece in or in the vicinity of their mouth and breathes into the mouthpiece. An inhaled breath flows in through inlet 46, through one-way valve 32 to the mouthpiece (and the user) and is exhaled through the mouthpiece and through the one-way inlet valve 40 into the device 20. The one-way valve 32 prevents any air flow out of the device through the inlet 46. Similarly, no flow can enter the device through the exhaled breath outlet 60 due to the one-way valve 40. The user provides the necessary pressure to push the breath through the device 20 thus achieving unassisted breath capture. Alternatively, a mouthpiece that can be placed in/around a human mouth without causing any substantial discomfort to the user may be used (e.g. as shown in FIG. 1*a*). The mouthpiece may be made of any suitable material, e.g. silicone and/or plastics. The mouthpiece may be detachable so that it can be changed after every use. Thus, beneficially, the same breath sampling device may be used by more than one user/patient.

In this arrangement, a tapered connection 34 can be present in the mouthpiece section, e.g. to facilitate connection of the mouthpiece. The connection 34 may itself be connected to a connector 36. The connector 36 is connected between the one-way valve 32 which controls flow of inhaled breath into the device and the second one-way valve 40 through which exhaled air passes to the rest of the device 20.

As shown in this arrangement, an optional breathing filter 44 may be connected between the connector 36 and the sorbent housing 50. The function of filter 44 may be to prevent bacteria and viruses entering the device when exhaling from passing through filter 44 to the sorbent material 52. The filter 44, for example, may thus beneficially prevent cross-contamination between patients when the breath sampling device is used by more than one user/patient. The breathing filter 44 may also beneficially aid both in condensation and water droplets removal. An advantage of including a filter is that any component downstream of the filter may be reused between patients.

As shown in this arrangement, a spirometer 54 may optionally be connected between the exhaled breath outlet 60 and the sorbent housing 50. The spirometer 54 is used to measure the volume of air passing through the outlet. When the device is used to collect multiple breaths, the spirometer 54 may be configured to measure the total volume of breath which has passed through the sorbent material. For example, it may be necessary for a threshold volume (e.g. 60 litres) to be sampled to ensure an accurate result. It is also noted that the threshold volume is a huge volume compared with the volumes typically sampled with known devices such as ReCIVA®. When a spirometer 54 (or other volume measuring device) is not used, the user may be instructed to breathe into the device for a fixed time limit (e.g. 7 minutes) to ensure that a threshold total breath volume (and hence the breakthrough volume) is reached. In this example, the amount of the specific compound which is captured by the sorbent material may be calculated by taking into account the time a user was breathing, e.g. by calculating mass/minute (or similar).

A second spirometer (not shown) may be included connected to inlet 46 to measure ventilation, the movement of air into the lungs of the user. Thus, beneficially, the second spirometer may be used to measure the lung capacity of the user/patient.

Figure 2C:
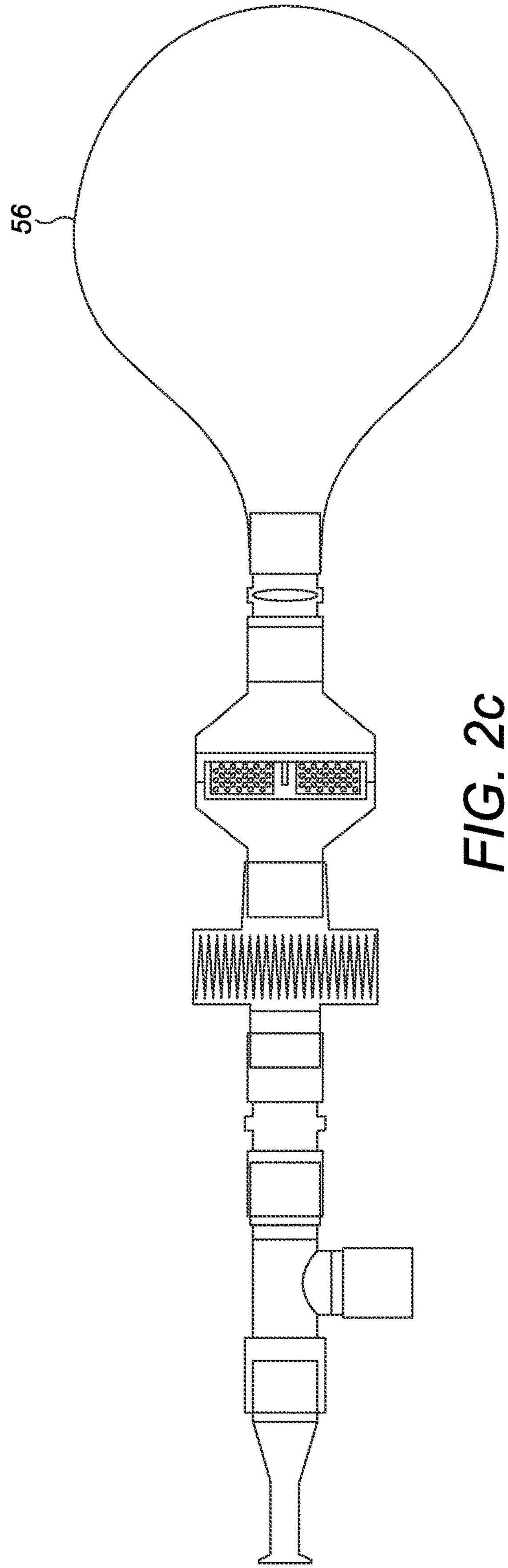
FIGS. 2*c* and 2*d* are variations of the breath sampling device of FIG. 2*a* in which an electronic spirometer is replaced with alternative non-electronic components.

FIG. 2*c* illustrates an alternative in which a mechanical indicator, e.g. an inflatable bag 56, may be used to indicate the total volume of breath which has passed through the sorbent material. The bag may have the correct threshold volume, e.g. 60 litres. A further one-way valve may also be incorporated to prevent air flow back into the device, although this additional one-way valve may not be needed because the functionality may also be provided by the existing one-way valve 40.

Figure 2D:
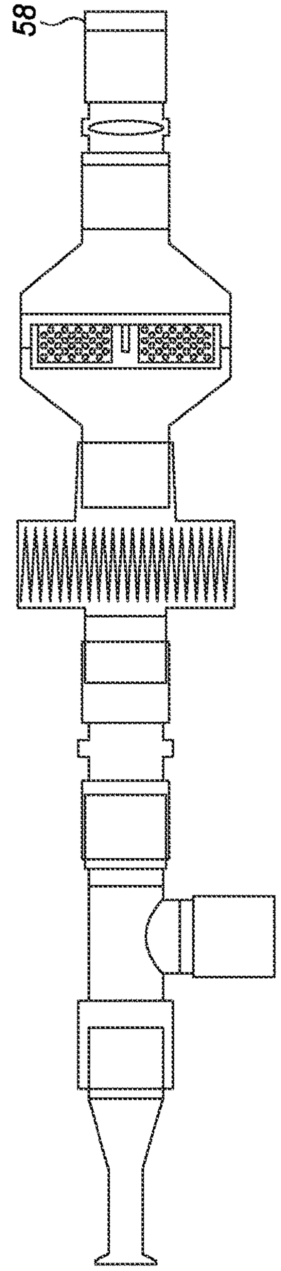

FIG. 2*d* illustrates an alternative in which a mechanical or chemical indicator, e.g. a colour change strip 58, may be used to indicate the total volume of breath which has passed through the sorbent material. The strip changes colour once the correct threshold volume of a detected compound, e.g. a certain amount of carbon dioxide, has passed over the strip. The skilled person will appreciate that any other similar indicator that detects chemicals may be used.

Figure 2E:
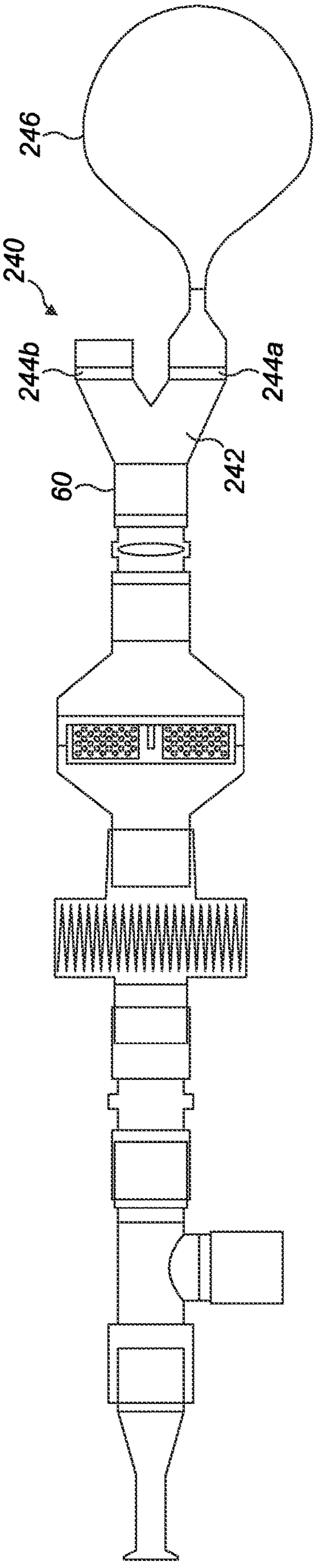
FIG. 2*e* is a variation of the breath sampling device of FIG. 2*c;*

FIG. 2*e* illustrates an example variation of the arrangement of FIG. 2*c* a smaller inflatable bag 246 to meter the exhaled volume. The device includes a splitter 242 which divides the flow from the exhaled breath outlet 60 into two flows. The splitter 242 in this example has a Y-shape but other shapes may be used. The splitter 242 comprises two one-way valves 244*a*, 244*b* each having different flow resistances. The first one-way valve 244*a* has a significantly lower flow resistance than the second one-way valve 244*b*, for example a ratio of 1:11. As a result of the lower flow resistance, initially exhaled breath passes through the first one-way valve 244*a* in preference to the second one-way valve and is collected in the inflatable bag 246.

As the bag inflates, the flow resistance through the first one-way valve 244*a* increases gradually until the flow resistance is higher through the first one-way valve than the second one-way valve 244*b*. Once the flow resistance through the first one-way valve 224*a* is higher than the second one-way valve 244*b*, any remaining airflow through the splitter 242 flows through the second one-way valve 244*b* to exit the device. The inflatable bag may for example be a 5-litre bag which together with a 1:11 split ratio on the Y-splitter means that once the bag is filled, it can be assume that at least 12 times the amount of exhaled breath has passed through the sorbent material. In other words, a total breath volume of 60 litres has been achieved. It will be appreciated that other sizes of bag and ratios of flow resistance on the valves can be used to ensure that filling the small bag indicates that the overall breakthrough volume has been achieved.

Returning to FIG. 2*a*, an orifice plate 62 may optionally be connected between the outlet 60 and the sorbent housing 50, more specifically in this arrangement between the outlet 60 and the spirometer 54 but the order may be changed. The orifice plate 62 is a plate with an orifice and is supported in an adaptor 42. The orifice will provide extra flow resistance along the fluid path between the exhaled breath inlet 30 and the exhaled breath outlet 60 to restrict the flow of air (from the user's breath) through the device. Typically, orifices produce a non-linear flow resistance. In other words, an orifice presents a disproportionally higher flow resistance at higher flow rates which helps keep the airflow and hence airspeed through the sorbent below acceptable limits, for different lung efforts. Thus, the device may be adapted for use across a wide range of patients and/or may be designed to achieve even more dramatic increases in flow resistance above some nominal flow value.

As explained in more detail below, the design of the orifice plate may be adjusted along with the geometry of the sorbent material to achieve the desired flow rate through the device. Different orifice plates may also be used based on clinical data to improve sampling performance and to make the more comfortable to breathe through for different types of patient. For example, a tall male could have a more restrictive orifice than a small female in order to keep the flow rate below a reasonable threshold.

Merely as an example, the sorbent material be disk shaped with a diameter of 17.2 mm and a thickness of 4.03 mm, thus containing 625 mg of Carbosieve SIII 60-80. This amount of sorbent produces a resistance of 18.9 mbar at 10 L/min. The orifice in the orifice plate may be 2.19 mm in diameter and the orifice plate may be within a tube having a diameter of 20 mm. At these dimensions, the orifice plate provides resistance of 32.3 mbar at 10 L/min. Alternatively, as another example, the sorbent material be disk shaped with a diameter of 21.9 mm and a thickness of 2.5 mm, thus containing 635 mg of Carbosieve SIII 60-80. This amount of sorbent produces a resistance of 5.4 mbar at 10 L/min. The orifice in the orifice plate may be 3.88 mm. At these dimensions, the orifice plate provides resistance of 33.4 mbar at 10 L/min.

The arrangement of the device shown in FIGS. 2*a* and 2*b* comprises a mouthpiece, a tapered connection 34, a connector 36 having two one-way valves 32, 40, a filter 44, a sorbent housing 50, a spirometer 54 and an orifice plate 62 which are fluidly connected to form a fluid pathway from the inlet 30 to the outlet 60. Although the device is unitary, it is also fully modular and one or more of the components, e.g. the filter 44, the spirometer 54 and the orifice plate 62 may be optionally omitted or swapped in order according to the design. One or more adaptors 42 may be used to facilitate connections between the different components. For example, the filter 44 is connected to the one-way valve 40 via an adaptor 42. Similarly, the orifice plate 62 is supported in an adaptor 42 connected to the spirometer 54. Any suitable adaptors 42 may be used. The function of the adaptor is to provide a simpler and/or more reliable connection between different components of the device. The skilled person will also appreciate that all of the parts of the device 20 conform to the appropriate standards, e.g. the ISO5356-1:2015 standard. The use of the adaptors allows sections of the device to be replaced or removed between use by patients, for example the connector 36, both one-way valves 32, 40, the filter 44 and the adaptor 42 upstream from the filter 44 may be replaced between patients.

Figure 3:
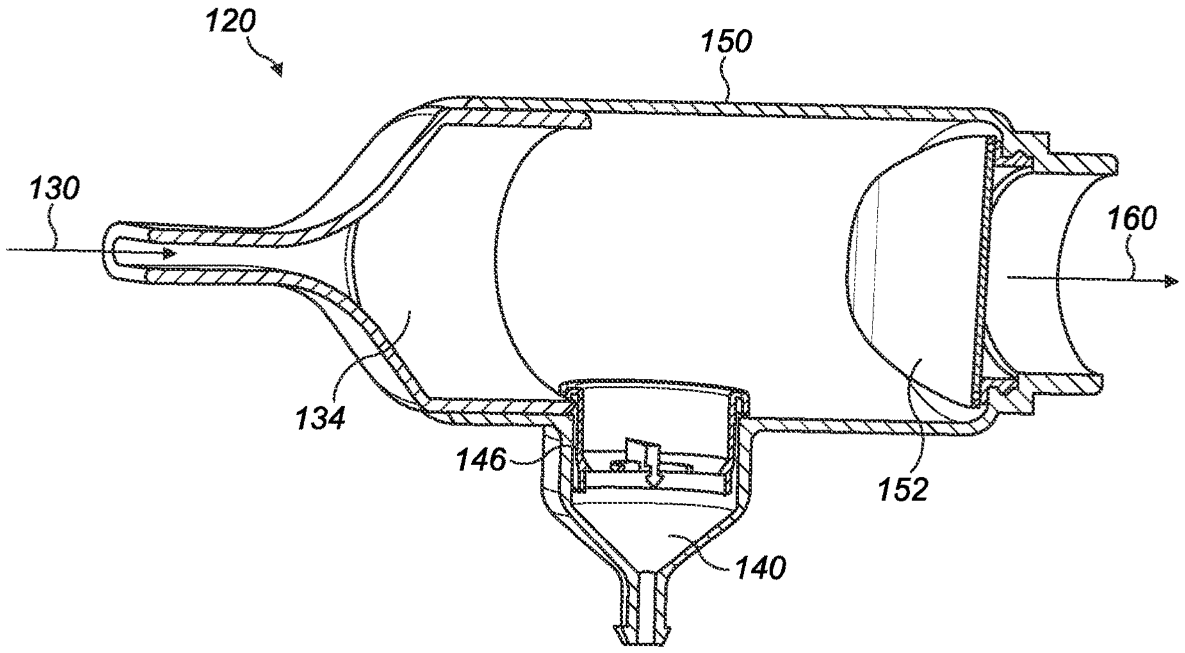
FIG. 3 is a cross-sectional view of another breath sampling device according to the techniques described in the present application.

FIG. 3 shows another arrangement of a suitable breath sampling device according to the invention which has fewer components than the arrangement of FIG. 2*a*. In this arrangement, the breath sampling device 120 comprises a housing 150 and an adsorber material holder 152 within the housing 150. The device comprises an inlet 130 and an outlet 160 which are fluidly connected by the housing 150 and the adsorber material holder 152 is supported on the fluid path between the inlet and the outlet to sample the breath of the user/patient. The inlet 130 is configured to accommodate the mouthpiece 134. In use, the breath airflow of the user can travel from the mouthpiece 134, via the housing 150 to the adsorber holder 152 and out the outlet 160. In this arrangement, the adsorber holder 152 is arranged so that air passes through the sorbent material in a direction which is generally parallel to the direction of flow of exhaled breath through the inlet.

In this arrangement, the housing 150 may be in the form of a cylindrical hollow tube. The housing 150 may be made of plastic or any suitable material. A bypass portion 140 extends from the housing 150, generally at right angles to the fluid path between the inlet 130 and the outlet 160. In this example, the bypass portion 140 comprises a flow switch to provide the mechanical separation of the different parts of a breath cycle as described above.

The bypass portion 140 provides a second outlet through which exhaled air may exit the device. The bypass portion 140 can be configured to mechanically fractionate the breath from a user whereby when the user breathes into the mouthpiece, the first part of the breath (perhaps 10%) preferentially exits the device via the bypass portion 140. The subsequent portion of the breath may flow along the fluid path to the sorbent housing 50 to be sampled. In this example, the bypass portion 140 projects generally at right angles to the fluid path between the inlet 130 and the first outlet 160.

The first portion of an exhaled breath does not typically contain air that has entered the alveoli and is just the air which sits in the mouth and bronchiolae (aka anatomical dead space). Thus, this first portion typically contains few particles to be sampled. The separating of the breath may be achieved mechanically, for example, by connecting the bypass portion 140 to an inflatable element such as a balloon or a bag. When a user first breathes into the mouthpiece 134, the deflated element provides little or no resistance to fluid flow and provides a lower resistance to fluid flow than the sorbent material. Accordingly, the first portion of the breath flows through the bypass portion 140 and begins to inflate the inflatable element. A one-way valve 46 may be connected to the inflatable element to stop fluid flowing back through the bypass portion 140. Once the inflatable element is at least partially or fully inflated, there is significantly more resistance to fluid flow and fluid flows more easily along the fluid path through the sorbent material. The capacity and elasticity of the inflatable element may be selected to ensure the desired separation of the exhaled breath. When the device is used to collect multiple breaths, the inflatable element may be vented between each breath.

It may also be possible to achieve a similar mechanical effect using other devices such as valves. Consequently, the bypass portion may be completely passive without any electronics. Thus, beneficially, the breath sampling device may be more durable and cheaper and easier to manufacture.

As illustrated, the adsorber holder 152 extends across the entire cross-section of the housing 150 and thus extends across the entire fluid path from inlet to outlet. The adsorber portion 130 comprises an adsorber material. By extending across the entire cross-section, as in FIG. 2, the breath sampling device is configured to sample the entire airflow of the breath in contrast to segments of the airflow which are directed towards the sorbent tubes of the known devices.

Figure 4A:
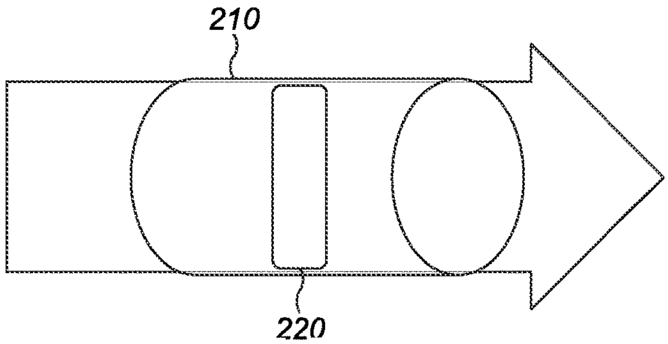
FIG. 4*a* is schematic simplified view of the breath sampling devices of FIGS. 2*a* to 3.

In the examples of FIGS. 2*a* to 3, the adsorbent material (and/or its holder) extends across the entire cross-section of the housing. Thus, as shown in FIG. 4*a*, the housing may be considered to be a large sorbent tube 210 containing sorbent material 220. As schematically illustrated by the arrow, exhaled breath passes through the tube 210 and is sampled by the sorbent material 220. Such an arrangement appears straightforward but simply using a standard shaped sorbent material 220 across a large sorbent tube would make the device too resistive to breathe through. For example, if we consider that a user typically exhales at 10 L/min, the pressure required for an exhaled breath to pass through the sorbent material 220 in a standard sorbent tube may be as high as 1100 mbar which is significantly higher than the 5.4 mbar at 10 L/min for the sorbent disk designed according to the present techniques. Furthermore, using large quantities of sorbent will drastically increase the cost associated with the device, particularly because sorbent is typically very expensive (40$/g). Accordingly, changing the geometry of the sorbent is not straightforward and a method to adapt the geometry of the sorbent is described below.

Figure 4B:
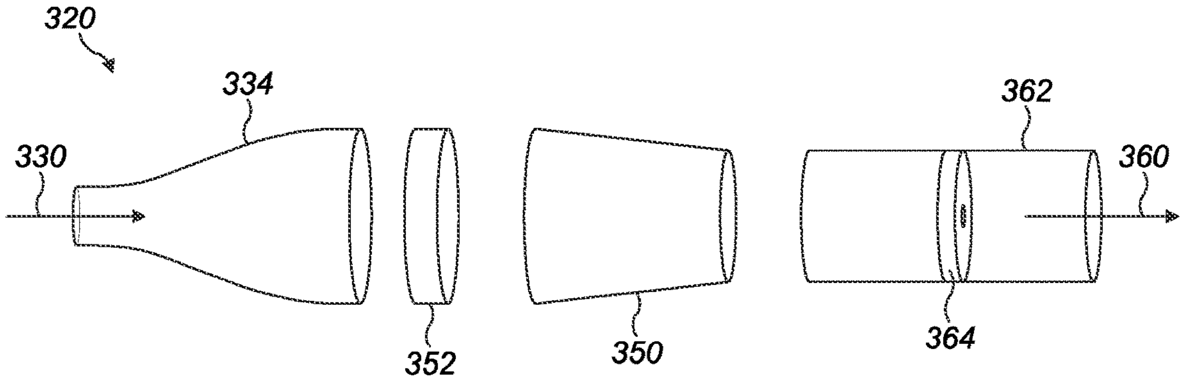
FIG. 4*b* is a schematic model which may be used to optimise the design of the breath sampling devices of FIGS. 2*a* to 3.

FIG. 4*b* shows a model of a breath sampling device 300 which can be used to design the geometry of the sorbent. The device 300 comprises an inlet 330 and an outlet 360. The inlet 330 is formed in a mouthpiece 334 which is connected to a sorbent housing 350 which is connected to an orifice plate holder 362. The mouthpiece, sorbent housing and orifice plate holder may be considered to form a three-part housing for the device. The sorbent housing 350 houses a sorbent material 352 which is modelled as a disk having the variable parameters: diameter, thickness and hence mass. As illustrated, the sorbent material 352 the mouthpiece portion 334 and the sorbent housing 350 may form a two-part housing for the sorbent. FIG. 4*b* may be considered to be a minimal version of the device with a mouthpiece, sorbent and orifice, and without a filter.

The orifice plate holder 362 supports an orifice plate 364 having an orifice. An orifice may be used when additional flow restriction is required but it is desired to avoid including more sorbent. The orifice plate holder 362 is modelled as a pipe, i.e. generally cylindrical and hollow. The effect of the orifice plate may be modelled using the following equations:

$$dP = \frac{1}{2\rho}(1-\beta^4)\left(\frac{Q_m}{C_d A}\right)^2$$

where dP is the pressure drop across the orifice, $\dot{Q}_m$ is the mass flow rate through the orifice, ρ is the nominal density of the fluid (which for air is 1.225 kg/m$^3$), A is the cross-sectional area of the orifice, and $C_d$ is the co-efficient of discharge (set to 0.62). The value β is defined below as:

$$\beta = \frac{d_{orifice}}{d_{pipe}}$$

where $d_{orifice}$ is the diameter of the orifice and $d_{pipe}$ is the diameter of the pipe (i.e. the holder 362) and has a value of 20 mm in the model examples.

Figure 5:
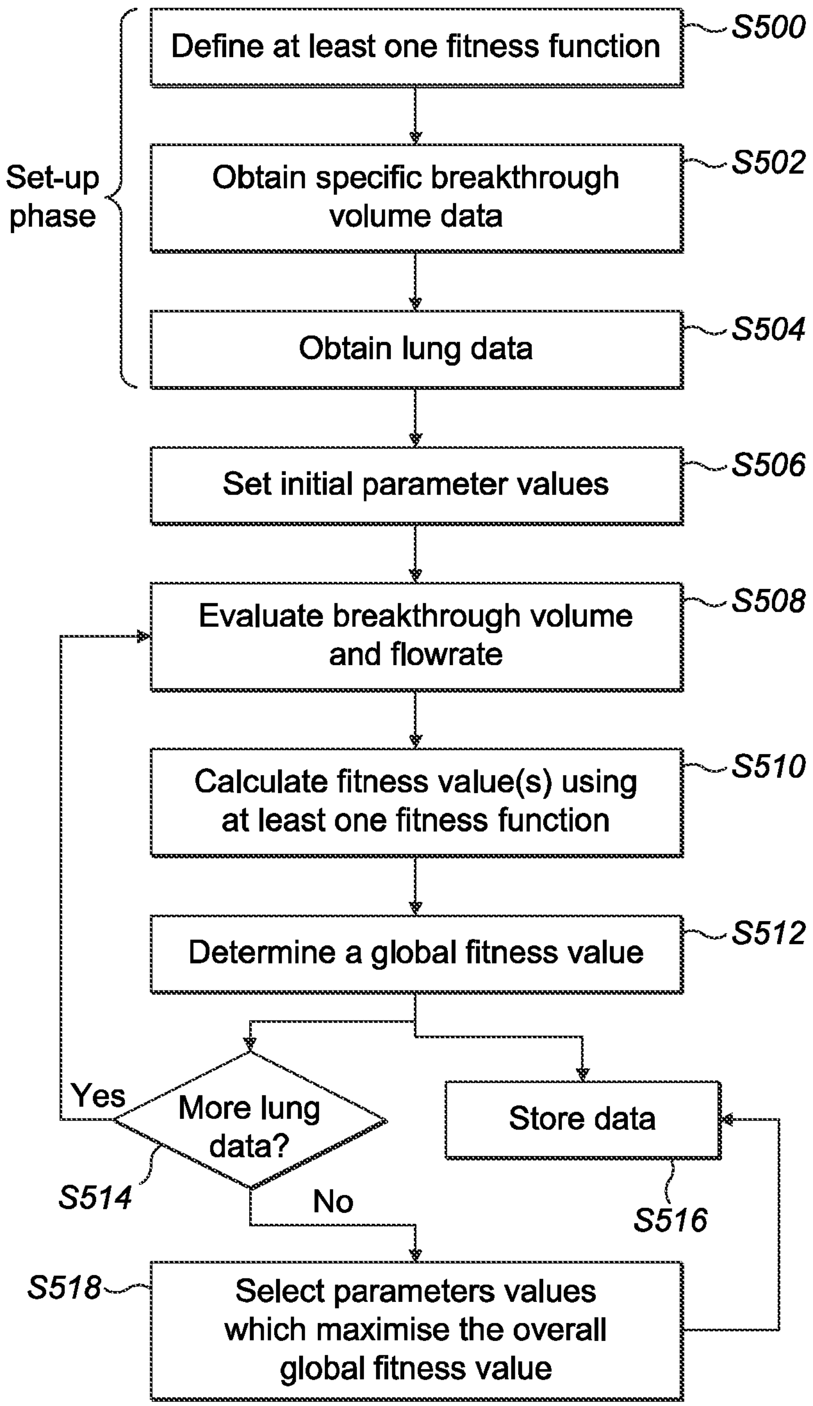
FIG. 5 is a flow diagram of the method of optimising the design of a breath sampling device, for example using the model of FIG. 4*b;*

FIG. 5 is a flowchart illustrating how the parameters of the sorbent material (including diameter and thickness/mass) together with the orifice diameter may be varied to optimise the design of the device. In a first step S500, at least one fitness function is defined to evaluate the fitness (i.e. suitability) of the design. FIGS. 6*a* to 6*e* illustrate examples of fitness functions which may be used. In each of these examples, the fitness varies between 0 and 1 with a fitness value of 0 indicating that the design is completely unacceptable and must be rejected. A fitness value of 1 indicates that the design is optimised, i.e. at the top of the range and completely acceptable.

An example of a suitable fitness function $f(x)$ is:

$$f(x) = \frac{1}{2}\text{erf}(s(x - x_o)) + 0.5$$

where x is the parameter being varied, and erf is the error function:

$$\text{erf}(x) = \frac{2}{\sqrt{\pi}}\int_0^x e^{-t^2}dt$$

s is the scale parameter defined as $$s = \frac{z_1 - z_o}{x_{ideal} - x_{unacceptable}}$$

where $x_{ideal}$ is the ideal value of the parameter such that $f(x_{ideal})=b$ (e.g. 0.9) and $x_{unacceptable}$ is the unacceptable value of the parameter such that $f(x_{unacceptable})=a$ (e.g. 0.1), and:

$$z_o = \text{erf}^{-1}(2(a - 0.5))$$

$$z_1 = \text{erf}^{-1}(2(b - 0.5))$$

$\text{erf}^{-1}$ is the inverse error function. $x_o$ is the location parameter defined as:

$$x_o = x_{ideal} - \left(\frac{Z_1}{s}\right)$$

As set out above, a fitness value of 0 indicates that the design is completely unacceptable and a fitness value of 1 indicates that the design is completely acceptable. In practice, rather than work to these extreme values, the design may take account of the ideal and unacceptable values for the fitness value (a and b, respectively). For example, a 98% error function may be considered with a=0.01 and b=0.99, respectively. A different error function, e.g. 95% or 99% could also be used. Two or more error functions may be combined, e.g. by multiplication, to provide more complicated/detailed fitness functions as described below.

Figure 6A:
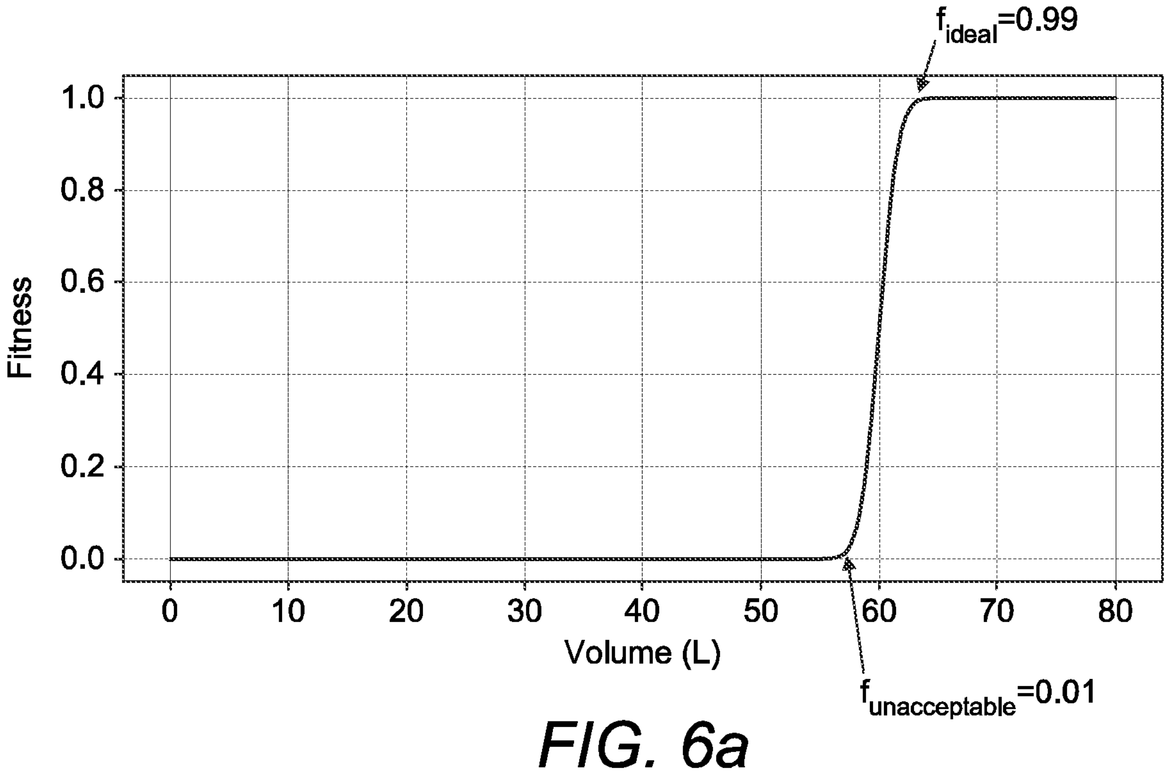
FIGS. 6*a* to 6*e* illustrates fitness functions plotting the variation of fitness value against total breath volume L, airflow (L/min), sorbent thickness (mm), sorbent diameter (mm) and sorbent mass (g), respectively.

FIG. 6*a* illustrates a fitness function showing how the fitness value varies with volume (litres) of breath collected. The total volume is the amount of breath which needs to be collected to correctly analyse the compound (compounds) within exhaled breath (i.e. to achieve the breakthrough volume). FIG. 6*a* plots an error function in which a device has a fitness value approaching 0 below a first total volume threshold (which represents a volume in which too little breath is sampled and thus breakthrough volume is unlikely to be achieved) and a fitness value approaching 1 once a second total volume threshold is exceeded (and breakthrough volume for the compound(s) of interest is likely to be achieved). In this example, the thresholds are both around 60 litres. The nature of the error function means that the fitness values are approaching 0 and 1, but may only achieve 0 and 1 for values of −infinity and +infinity respectively. Thus, using the formulas defined above, the ideal value of total breath volume which provides a fitness value of 0.99 may be $x_{ideal}$=63. Similarly, the unacceptable value of total breath volume which provides a fitness value of 0.01 may be $x_{unacceptable}$=57. In this example, $x_{unacceptable}$ is lower than $x_{ideal}$ and may alternatively be termed $x_{minimum}$.

Figure 6B:
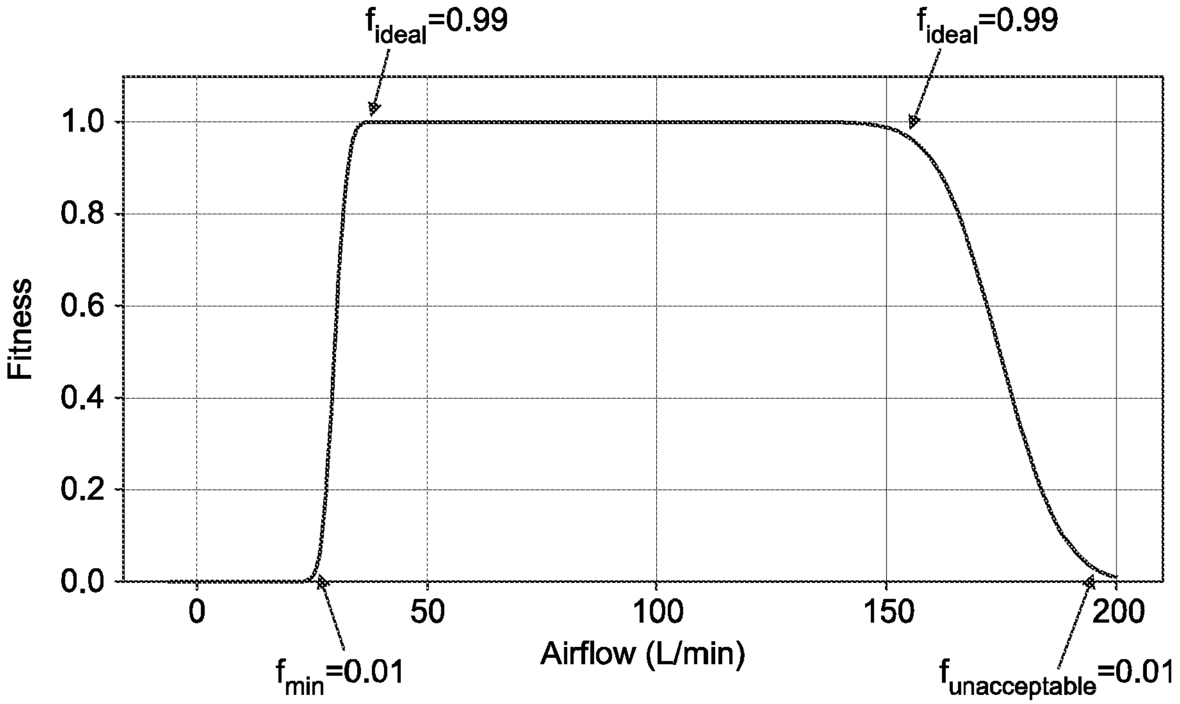

FIG. 6*b* illustrates a fitness function showing how the fitness value varies with airflow (litres/min). The device must be easy to breathe through for all subjects. FIG. 6*b* is a combination of two error functions: in the first error function, the device has a fitness value approaching 0 below a first airflow threshold and a fitness value approaching 1 once a second airflow threshold is exceeded with a smooth curve between the two thresholds and in the second error function, the device has a fitness value approaching 1 below a third airflow threshold and a fitness value approaching 0 once a fourth airflow threshold is exceeded with a smooth curve between the third and fourth thresholds. In this example, the two error functions are multiplied together. For the first error function, $x_{unacceptable}$=25, $x_{ideal}$=35 and for the second error function, $x_{unacceptable}$=200, $x_{ideal}$=150. In other words, a range of ideal values for airflow is defined as being between 35 and 150 L/min and the ranges for unacceptable values for airflow are below 25 and above 200 L/min.

Figure 6C:
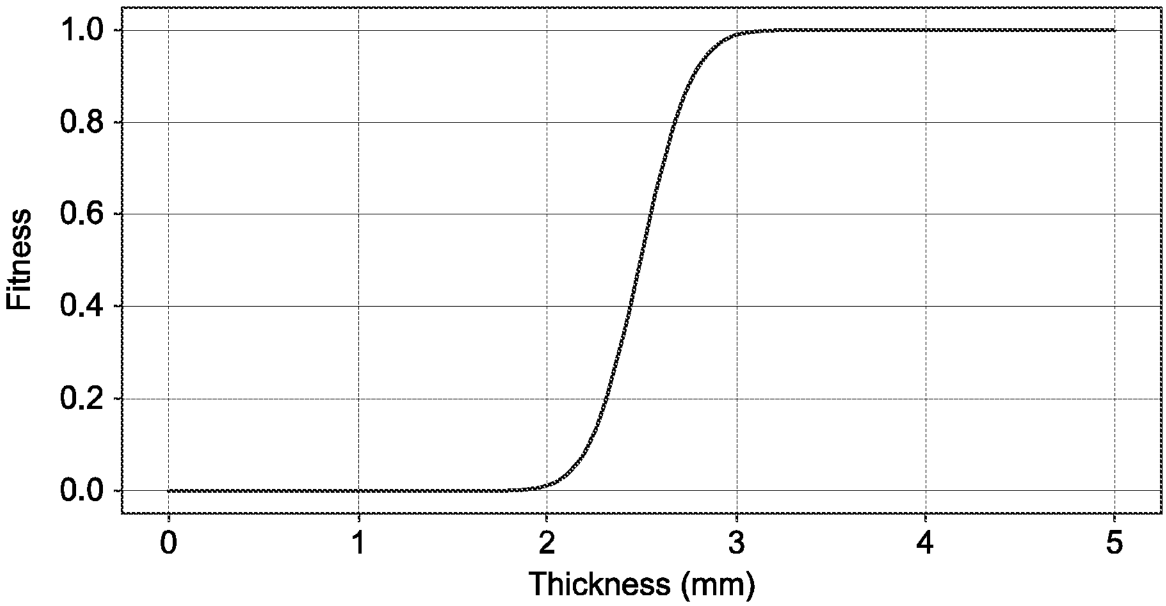

FIG. 6*c* illustrates a fitness function showing how the fitness value varies with thickness of the sorbent material. The sorbent must be thick enough to be mechanically suitable; for example, making a thin disk which does not bow or bulge is mechanically challenging. FIG. 6*c* is also an error function in which a device has a fitness value approaching 0 below a first thickness threshold and a fitness value approaching 1 once a second thickness threshold is exceeded with a smooth curve between the two thresholds. The first threshold is indicative of the minimum thickness of the sorbent material for it to be robust enough to incorporate in a design. Above the second threshold, there is no further mechanical advantage in increasing the thickness. In this example, the minimum thickness is 2 mm and the second threshold is 3 mm. Using the formulas defined above, the ideal value of the thickness which provides a fitness value of 0.99 may be $x_{ideal}$=3 mm. Similarly, the unacceptable value for the thickness which provides a fitness value of 0.01 may be $x_{unacceptable}$=2 mm.

Figure 6D:
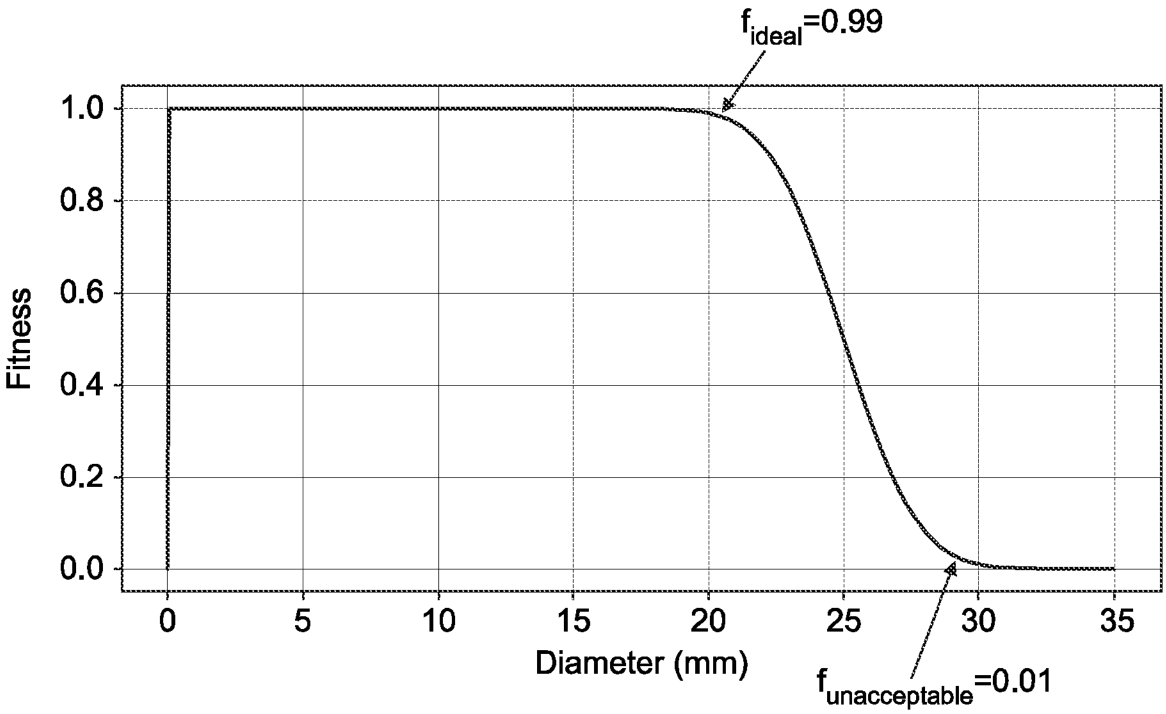

FIG. 6*d* illustrates a fitness function showing how the fitness value varies with diameter of the sorbent material. The sorbent material must not be too large for a practical design. FIG. 6*d* is also an error function in which a device has a fitness value approaching 1 below a first diameter threshold and a fitness value approaching 0 once a second diameter threshold is exceeded with a smooth curve between the two thresholds. In this example error function, $x_{ideal}$ is smaller than $x_{unacceptable}$ and may be termed $x_{maximum}$. The curve may be considered to mirrored horizontally around the point where y=0.5 when compared to the curves of FIG. 6*a* or 6*c*. In this example, $x_{ideal}$ is 20 mm and $x_{unacceptable}$ is 30 mm.

Figure 6E:
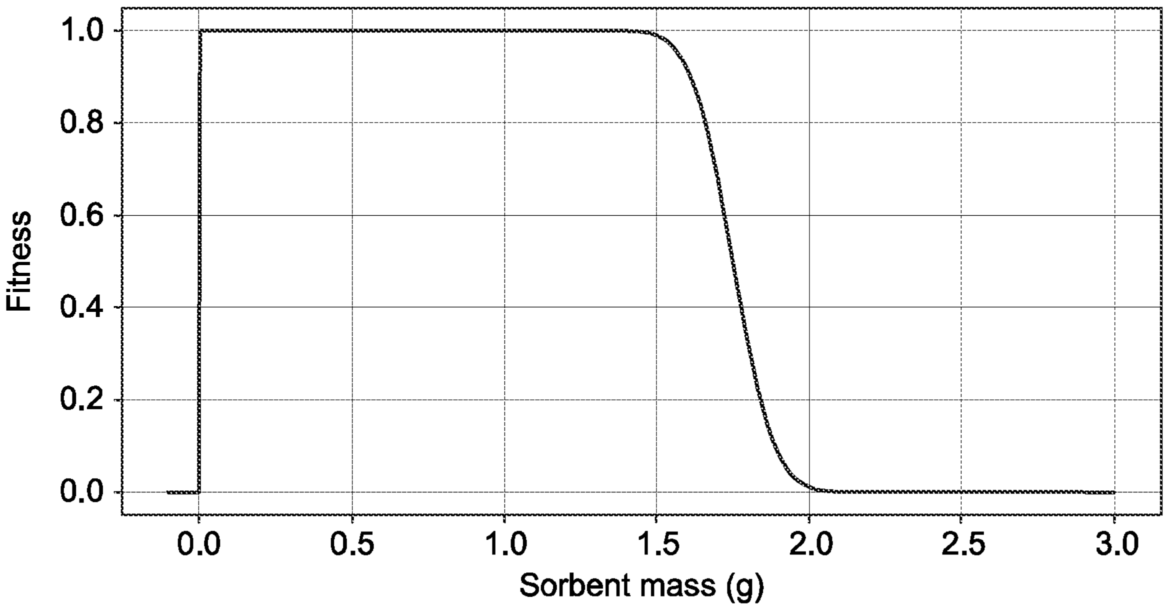

FIG. 6*e* illustrates a fitness function showing how the fitness value varies with mass of the sorbent material. Like FIG. 6*d*, FIG. 6*e* is also an error function in which a device has a fitness value approaching 1 below a first threshold and a fitness value approaching 0 once a second diameter threshold is exceeded with a smooth curve between the two thresholds. It will be appreciated that other implementations may be used to reflect the cost considerations of the manufacturer. For example, a more complicated fitness function may be used to reflect that generally a lower amount of sorbent material is preferred for cost reasons but there must be sufficient sorbent material for an accurate sampling. In this example error function, $x_{ideal}$ is 1.5 g and $x_{unacceptable}$ is 2.0 g.

Figure 7A:
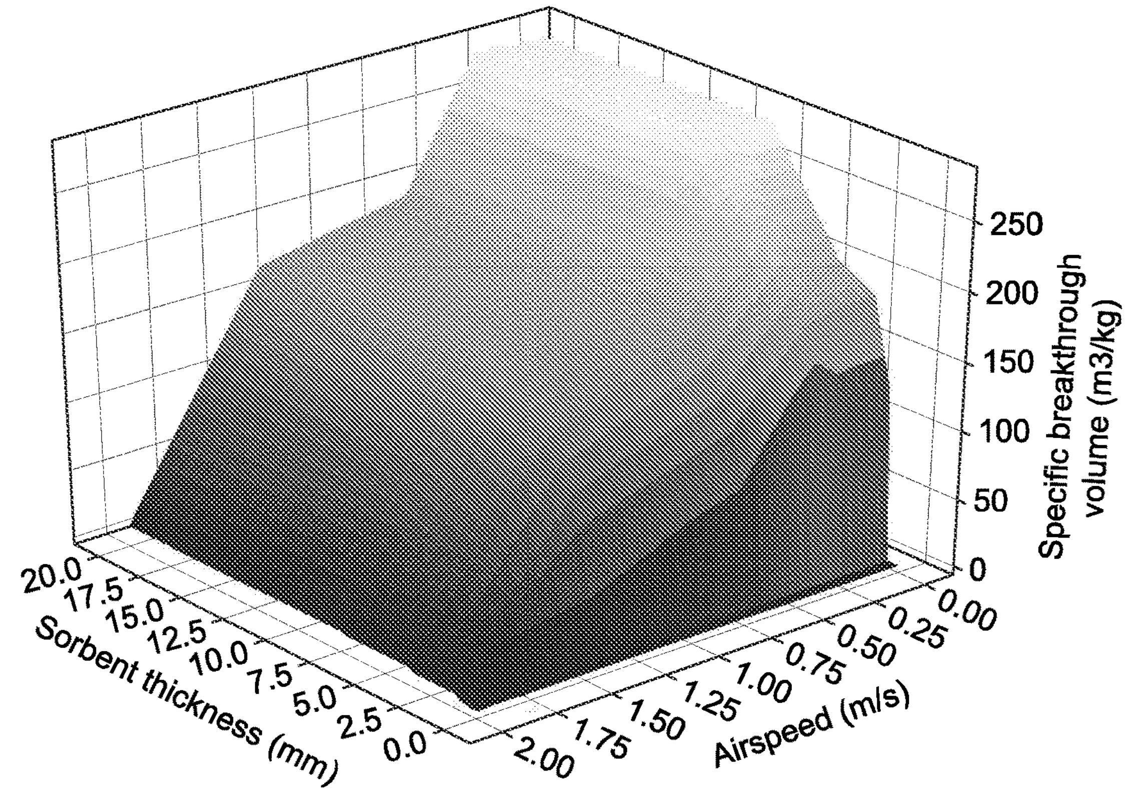
FIG. 7*a* plots the variation of specific breakthrough volume ($m^3$/kg) measured for different values of sorbent thickness (mm) and airspeed (m/s)

Returning to FIG. 5, the next illustrated step S502 is to obtain breakthrough volume data for the sorbent material. The step is shown sequentially but may be carried out before or in parallel with step S500. The breakthrough volume depends on airspeed, thickness and humidity. For example, halving the sorbent thickness decreases the breakthrough volume by more than half and doubling the sorbent area may completely change the breakthrough volume. For instance, humidity can be taken into account by calculating what percentage of the sorbent material will be effectively inactivated by the water in the breath, under a specific set of conditions, and hence what percentage of sorbent material is available to capture the compound of interest. This reduction in sorbent material available to capture the compound of interest manifests itself as a reduction in the breakthrough volume. This can be countered by altering other parameters, such as increasing the bed depth of the sorbent material. FIG. 7*a* illustrates the variation in specific breakthrough volume (breakthrough volume per unit mass of the sorbent) for different thicknesses of sorbent (mm) and airspeed (m/s). Each sorbent material will have a different specific breakthrough volume which is specific to the material being used and to the humidity of the airflow. The variation shown in FIG. 7*a* is the specific data which was measured using a sorbent material termed carbosieve SIII 60-80 by passing ethanol through the material. FIG. 7*a* shows that the relationship is complex. For example, it is noted that there is asymptotic behaviour for both low airspeed and thick sorbent but typically the device described in these examples operates at high airspeed and with a thin sorbent. It is noted that operating at high airspeed with a thin sorbent mean that the device is operating away from the usual parameters of standard sorbent tubes which have thicker sorbents.

As set out above, breakthrough volume thickness depends on thickness and this relates to the number of particles stacked in that thickness. The number of particles for a sorbent disk of a particular material and particular thickness can be calculated. For example, for a sorbent disk of approximately 4.03 mm made from Carbosieve SIII 60-80 there are approximately 23 particles. In other words, airflow passing through the disk can contact 23 particles as it passes through the disk. A breath needs to contact the surface of each particle of sorbent to be sampled. If the disk is thinner, there are fewer particles for the airflow to find a channel around. Thus it is more likely that a breath may find a channel through the sorbent material in which the breath avoids contacting any particles and avoids being sampled. The efficacy of the device is thus likely to be impacted adversely. The channeling of the airflow through the sorbent material is another reason why changing the geometry of the sorbent material is not straightforward. A thinner disk would be easier to breathe through but the number of particles which are stacked is smaller.

Figure 7B:
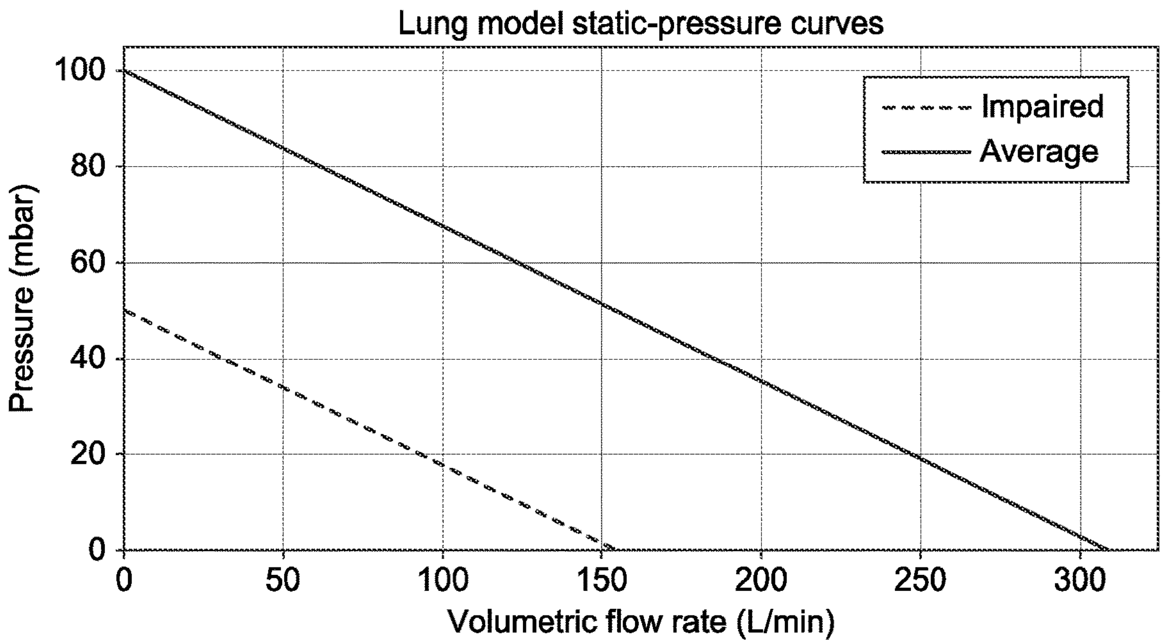
FIG. 7*b* shows a theoretical lung static pressure curves in volumetric flow rate (L/min) against pressure (mbar) generated by an impaired patient (lower line) and a typical user (upper line)

Returning to FIG. 5, the next illustrated step S504 is to obtain lung data. The step is shown sequentially but may be carried out before or in parallel with steps S500 and/or S502. The three steps may be considered to be a set-up phase of the method. FIG. 7*b* illustrates a theoretical lung-static pressure curve which is an example of lung data which may be obtained. Lung static pressure function is a function of pressure (mbar) vs volumetric flow rate (L/min). Two different lung loads are included: "average user" (x intercept is 100 mbar, y intercept is 309 L/min) and "impaired user" (x intercept is 50 mbar, y intercept is 154.5 L/min). The skilled person will appreciate that lung compliance curves/data can be used instead to give a more accurate model for the lung but static pressure is simple to implement and is thus illustrated in this example.

In order to achieve high efficiency of the breath sampling device, the diameter and thickness of the sorbent material may be varied and optionally the orifice diameter may be varied when an orifice plate is used as described above. These variables are determined in the optimization phase of the method but at step S506, initial values for the parameters need to be set. For example, the initial parameter values may be randomly selected by a monte carlo-method because this is a highly non-linear optimisation problem.

As an illustration, the monte carlo method may use 10,000 random numbers to sample from the following:

sorbent disk diameter ¢: 5 mm to 35 mm, logarithmically (base 10) spaced.

sorbent mass m: 10 mg to 2000 mg, logarithmically (base 10) spaced.

orifice diameter R: 1 mm to 20 mm, logarithmically (base 10) spaced.

The highest fitness of all the guesses above is used as the initial value in the optimisation step. In one example, the monte-carlo analysis yielded initial values of: 25.1 mm diameter sorbent disc, 870 mg of sorbent and 4.39 mm orifice diameter.

The next step S508 is to calculate the breakthrough volume $V_B$ and the flowrate dV/dt using an appropriate mix of empirically obtained data/relationships and theoretical formulae. For example, first flow resistance through the sorbent material may be calculated from the sorbent geometry and the sorbent flow resistivity (a constant), for example using the following equation:

$$R = \frac{\rho L}{A}$$

where R is the flow resistance (Pa s/m$^3$), ρ is the flow resistivity (Pa s/m$^2$), L is the length of sorbent channel (m), and A is the cross-sectional area of sorbent (m$^2$). Flow resistivity is a geometric property, e.g. particles of a certain size packed tightly should have the same flow resistivity. In practice it may change slightly due to the roughness of the sorbent granules and packing. Thus, theoretical values such as flow resistance can also be used in the calculations.

Next the air flow (also termed flowrate dV/dt or $\dot{Q}$) is determined using the calculated flow resistance together with the orifice geometry (see equation above) and the lung data obtained in step S504. This may be considered to be a relatively complex equation because it calculates the intersection (operating point) of the lung static pressure curve along with the sorbent resistance and orifice resistance load line (which is non-linear). For example, the airflow $\dot{Q}$ in which $P_{lung}(\dot{Q})=P_{total}(\dot{Q})$ may be calculated from:

$$dP_{sorbent} = R_{sorbent}\dot{Q}$$

$$dP_{orifice} = \frac{1\rho}{2}(1-\beta^4)\left(\frac{\dot{Q}}{C_d A}\right)^2$$

-continued $$P_{total}(\dot{Q}) = dP_{sorbent}(\dot{Q}) + dP_{orifice}(\dot{Q})$$

$$P_{lung}(\dot{Q}) = \text{P\_max} - \frac{P_{max}}{\dot{Q}_{max}}\dot{Q}$$

where $\dot{Q}$=volumetric flow ($m^3$/s or L/min), $P_{max}$ and $\dot{Q}_{max}$ are the value pairs found using the lung static pressure curves $P_{lung}$ of FIG. 7*b*, and $P_{total}$ is the total system response pressure (pressure vs airflow for the sorbent and orifice). Note that $P_{orifice}$ is not the same equation defined above for the orifice plate because the former was defined as mass flow and this is volumetric flow.

The airspeed is then calculated from the airflow, using a standard formula, e.g.

$$v = \frac{\frac{dV}{dt}}{A_{sorbent}}$$

where $A_{sorbent}$ is the cross-sectional area of the sorbent. It is noted that it is not the airspeed through the sorbent which can change locally.

The specific breakthrough volume (in Litres) is then linearly interpolated from the actual measurements such as those shown in FIG. 7*a* together with the calculated airspeed and sorbent thickness. Once the specific breakthrough volume ($L/g_{sorbent}$) is obtained, the breakthrough volume $V_B$ may be calculated by multiplying the interpolated value by the mass of the sorbent material.

Once the breakthrough volume and flow rate are calculated, the fitness functions defined in step S500 are used to obtain the fitness value for each parameter being considered (step S510). Thus, in this example, fitness values are calculated for each of breakthrough volume $V_b$; flowrate dV/dt; sorbent thickness t, sorbent diameter Ø and sorbent mass-m. Orifice diameter may be included in the airflow calculations as explained above. It will be appreciated that other fitness values may also be included, e.g. for sorbent resistance. Each of the individual fitness values is then used to calculate global fitness for the particular selection of design features (step S512). Any suitable calculation may be used, for example global fitness $f_{global}$ may be calculated as a geometric mean of all of the individual fitness values, i.e.

$$f_{global} = \sqrt[5]{f_{V_B} f_{\frac{dV}{dt}} f_t f_{\emptyset} f_m}$$

where $f_{V_B}$ is the fitness value for breakthrough volume, $f_{dV/dt}$ is the fitness value for flowrate, $f_t$ is the fitness value for sorbent thickness, $f_{\emptyset}$ is the fitness value for sorbent diameter, and $f_m$ is the fitness value for sorbent mass. It is possible to adjust the importance of each individual fitness when calculating the global fitness value, e.g. by using a weighted product with more important individual fitness values having higher weights than less important individual fitness values. By using geometric mean (or similar product) if any one of the fitness values is 0, the global fitness value is 0 because not meeting any one of the criteria means that the design is unacceptable.

An optional extra step S514 is to determine whether there is any additional lung data. For example, as shown in FIG. 7*b*, there are two lung load lines illustrated to reflect the fact that the device uses a person's own breath to push air through the sorbent material. Thus, in the first iteration, the individual and global fitness functions may be calculated for an average person, e.g. using the upper line in FIG. 7*b*. In this example, there is additional lung data for a "impaired" person (i.e. someone with weak lungs). Thus, the process loops back to step S508 to update the value of the flowrate/breakthrough volume in light of the new lung data. The individual fitness values calculated in step S510 are updated in light of the new information as are the global fitness value calculated in step S512. Both the global fitness value and the individual fitness values are calculated for each set of lung data. An average (or typical) person is likely to be able to push air through the sorbent material at a much higher speed than an impaired person which will reduce the breakthrough volume. Optimising the geometry for all patients and exceeding the minimum breakthrough volume is thus desirable. If there is no further lung data, the final step can be carried out using an overall global fitness value determined from each set of lung data. For example, the global fitness value for all sets of lung data may be calculated by averaging the global fitness values for each set of lung data, e.g. using geometric mean.

The final step illustrated in FIG. 5 is the optimisation step in which the optimal parameter values which maximise the overall global fitness value are selected. Any suitable optimisation may be used, for example the "Nelder-Mead" algorithm as described in Gao, F., Han, L. Implementing the Nelder-Mead simplex algorithm with adaptive parameters; Comput Optim Appl 51, 259-277 (2012). Although this is illustrated as a single step, it will be appreciated that this is typically an iterative process in which an optimisation algorithm converges on an optimal solution. For example, up to 1000 iterations may be needed to maximise the global fitness. In this example, the monte-carlo analysis yielded initial values of: 25.1 mm diameter sorbent disc, 870 mg of sorbent and 4.39 mm orifice diameter. Such an arrangement has a global fitness of 0.674. The initial value of the thickness can be calculated from the diameter and the mass. In one example, the optimisation step in S518 yields optimized values of 25.6 mm diameter sorbent disc, 1078 mg of sorbent, 3.12 mm thickness sorbent disc and 5.05 mm orifice diameter. This optimized arrangement has a global fitness of 0.787, indicating the optimization process increased the suitability of the parameters. The optimized values are output and as shown may be stored alongside any data stored earlier in the process. A breath sampling device may then be made using the optimized values.

Merely an illustration, the optimisation process using the Nelder-Mead algorithm ran through 75 optimization evaluations to determine the optimised values noted in the paragraph above. The tables below show the fitness values for this optimised arrangement:

| Parameter | Fitness Value |
|---|---|
| Breakthrough Volume | 0.996 |
| Airflow | 0.792 |
| Thickness of sorbent | 0.998 |
| Diameter of sorbent | 0.383 |
| Mass of sorbent | 1.0 |
| Global | 0.787 |

The values above show that the optimised disk is a little larger than desired because the fitness value for the diameter is relatively low. Additionally the airflow fitness value is not close to 1 indicating some compromise. The values of the intermediate data (e.g. pressure, flow rate, breakthrough volume, etc) which are calculated in the process are shown below too and emphasise the point above. For a normal patient, the threshold breakthrough volume is only just exceeded. For an impaired patient the flow rate is in between the minimum 25 L/min and ideal 35 L/min

| Parameter | Value for "impaired" patient using static pressure curve above | Value for "normal" patient using static pressure curve above |
|---|---|---|
| Static pressure (P) | 50 mbar | 100 mbar |
| Static flow rate (dV_dt) | 154.5 L/min | 309 L/min |
| Pressure (P) | 40 mbar | 83 mbar |
| Flow rate (dV_dt) | 30.7 L/min | 51.6 L/min |
| Airspeed (v) | 0.99 m/s | 1.67 m/s |
| Breakthrough volume (BV) | 154.4 L | 63.1 L |

Additional data for the optimised disk is provided below:

| Parameter | Value | Conditions |
|---|---|---|
| Sorbent resistance | 6.0 mbar | @10 L/min |
| Orifice resistance | 1.2 mbar | @10 L/min |
| Total resistance | 7.3 mbar | @10 L/min |
| Orifice diameter | 5.11 mm | |
| Pipe diameter | 20 mm | |
| Orifice airspeed | 42 m/s | |

Figure 8A:
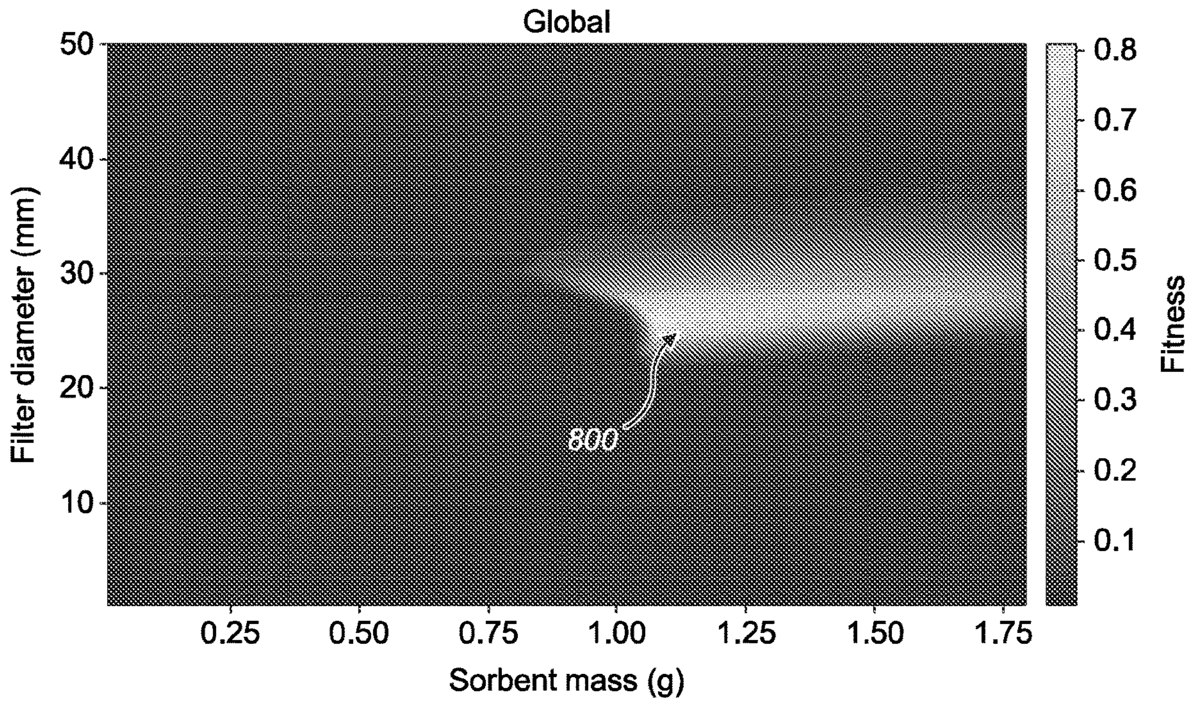
FIG. 8*a* is a heat map showing global fitness values for different values sorbent mass (g) and sorbent diameter (mm)
Figure 8B:
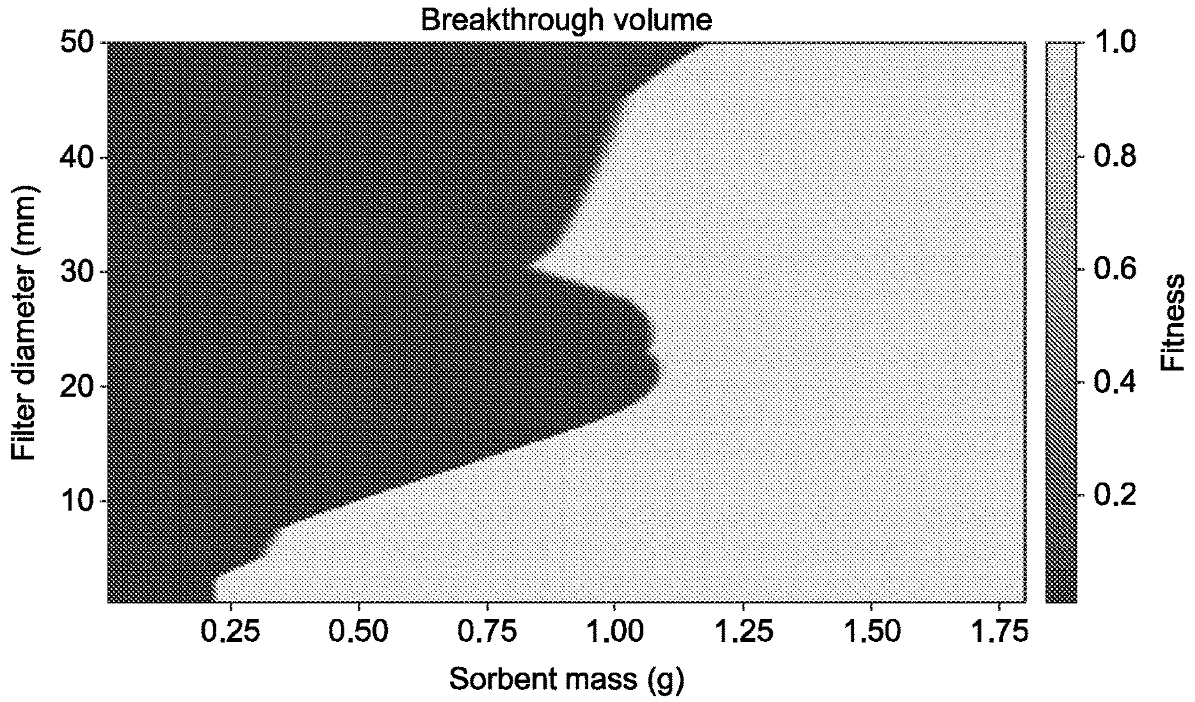
FIGS. 8*b* to 8*g* are heat maps plotting the variation of different individual fitness values with respect to two parameters: filter (i.e. sorbent) diameter and sorbent mass.

As an alternative to an iterative optimisation process, the parameter values which optimise the global fitness value may be obtained from a database such as that graphically represented in FIGS. 8*a* to 8*g*. The database could be generated using the models described in relation to FIG. 4*b* to calculate the individual fitness values (and hence global fitness value) for a large number of values of sorbent disk diameter, thickness and mass, and orifice diameter. The optimal value can be found by indexing through the database. FIG. 8*a* plots the variation of global fitness with two parameters: filter (i.e. sorbent) diameter and sorbent mass. Thus, in this optimisation space, other parameters such as the orifice diameter are considered to be fixed. FIG. 8*a* can thus be considered to depict a slice from a 3D database. The highest global values are found in the area labelled 800 with diameters between 24 to 28 mm and mass of between 1.05 g to 1.15 g. These values correspond to those identified above using the optimisation algorithm. However, the values are limited by the resolution and/or size of the database.

Figure 8C:
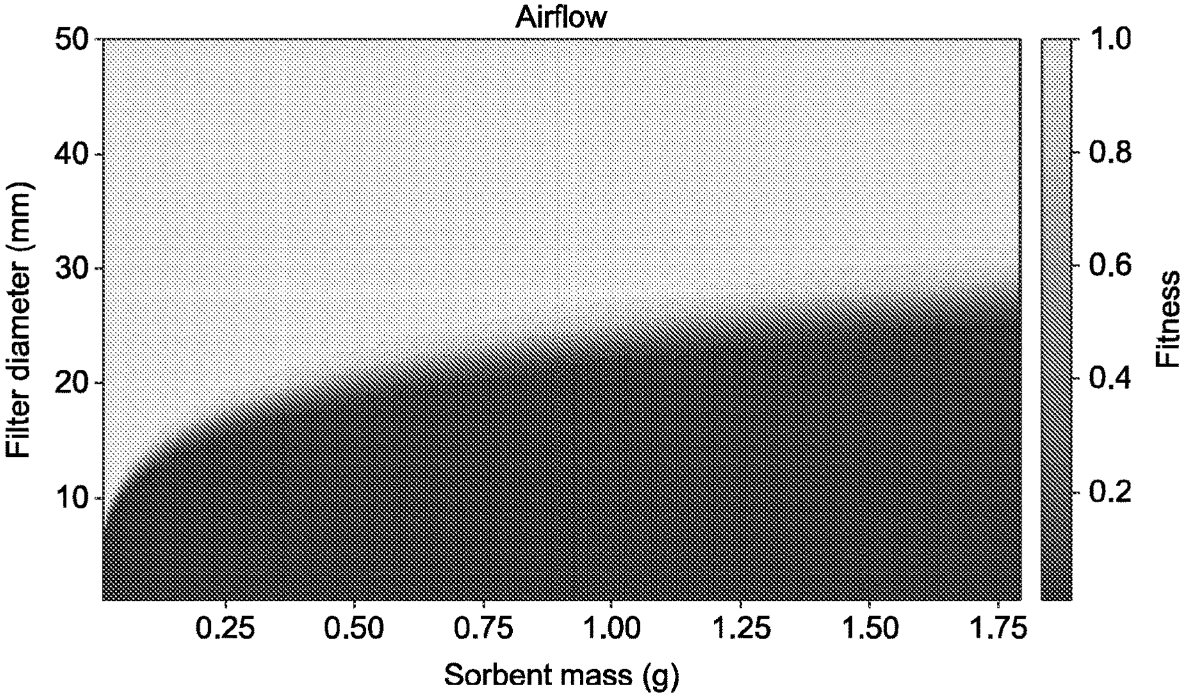
Figure 8D:
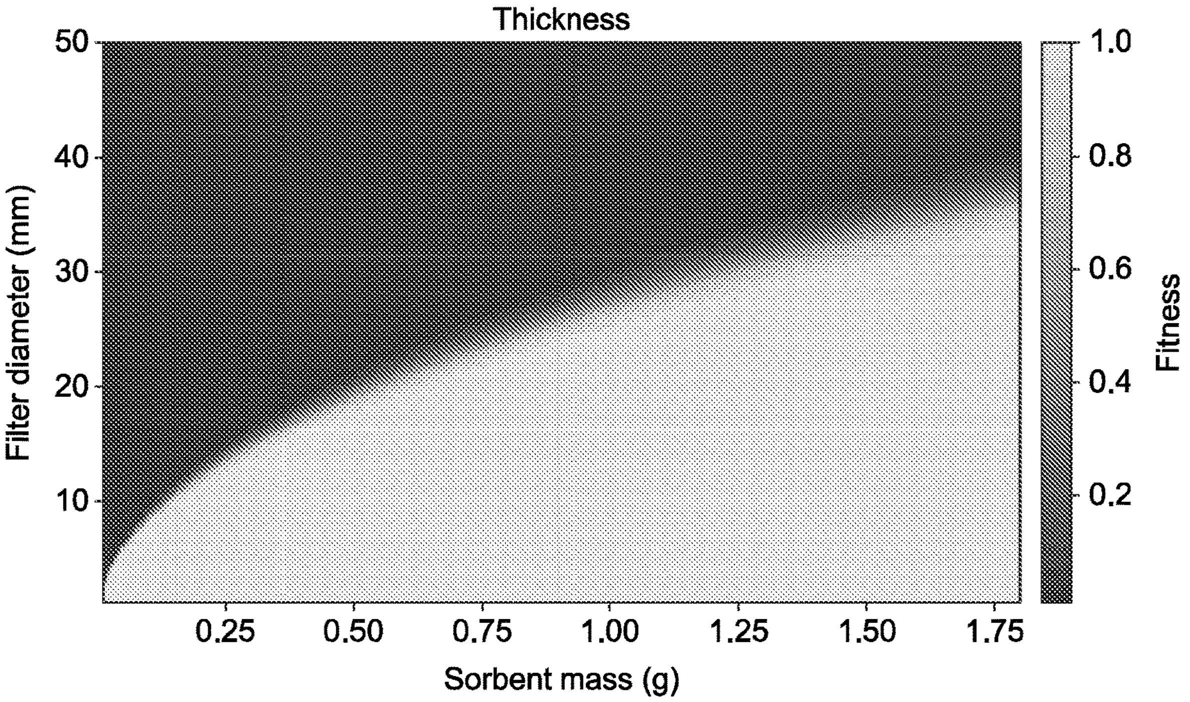
Figure 8E:
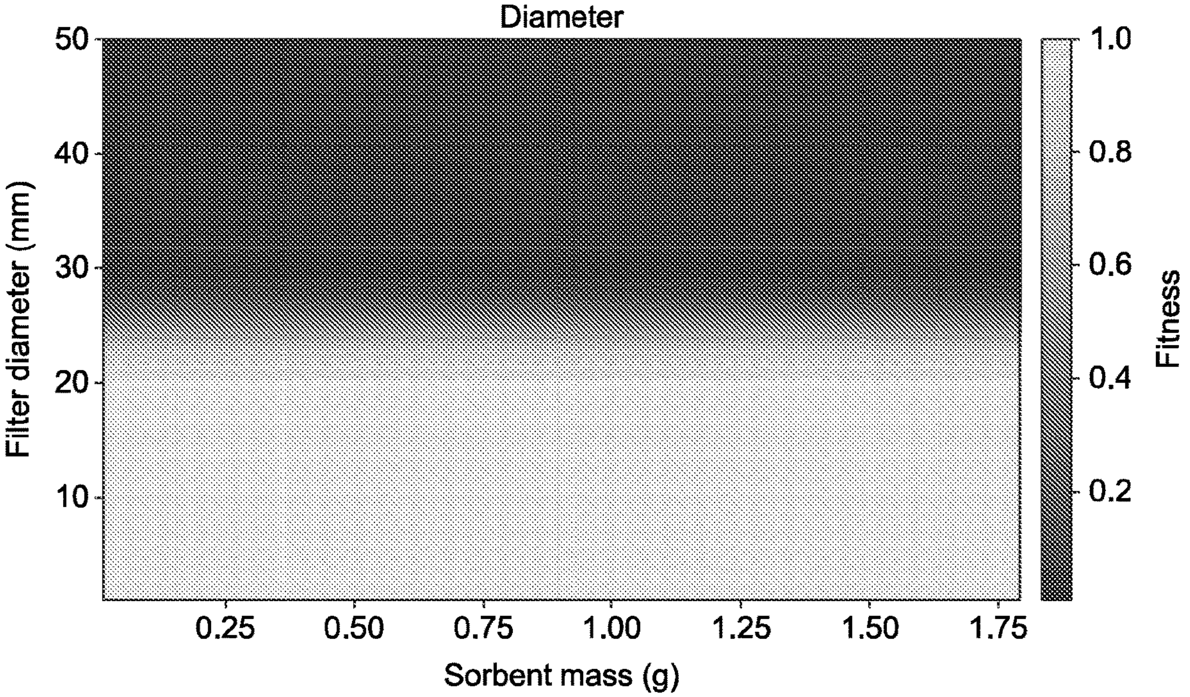
Figure 8F:
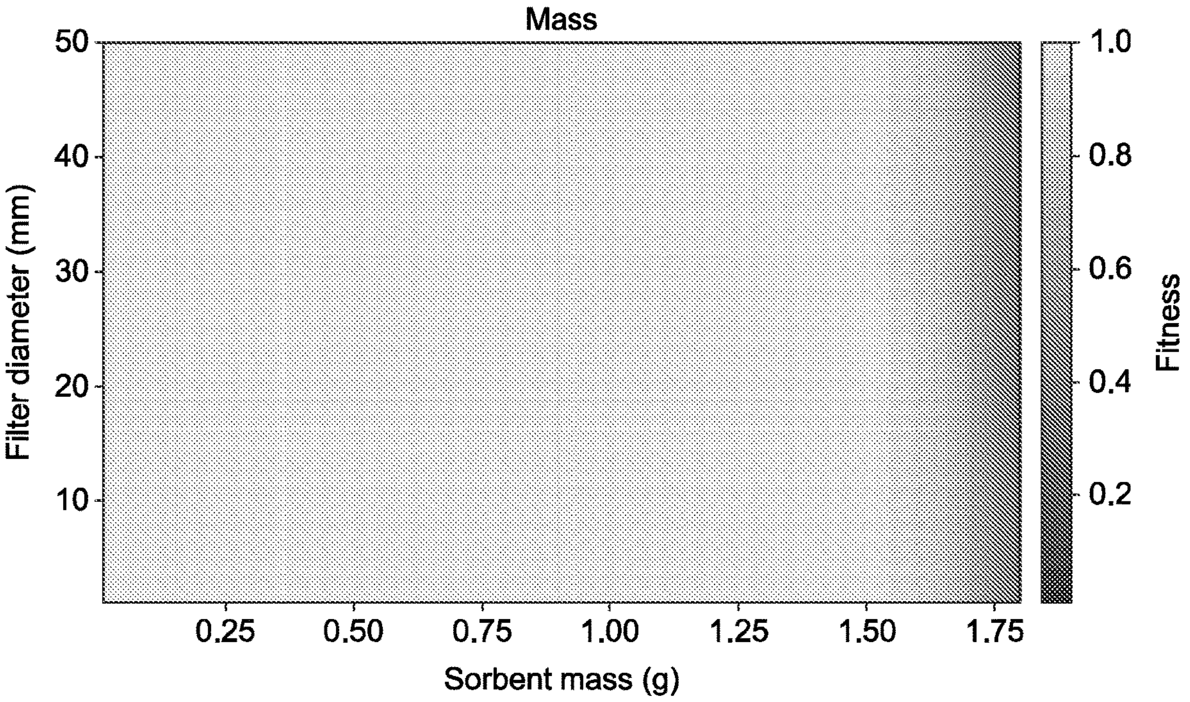

FIGS. 8*b* to 8*f* show other plots which may form part of the database. For example, FIGS. 8*b* to 8*f* plots the variation of each individual fitness value with respect to two parameters: filter (i.e. sorbent) diameter and sorbent mass. Following the order shown in FIGS. 6*a* to 6*e*, FIG. 8*b* plots the variation of the fitness value for the breakthrough volume, FIG. 8*c* plots the variation of the fitness value for the airflow, FIG. 8*d* plots the variation of the fitness value for the thickness of the sorbent, FIG. 8*e* plots the variation of the fitness value for the diameter of the sorbent, and FIG. 8*f* plots the variation of the fitness value for the mass of the sorbent.

Figure 8G:
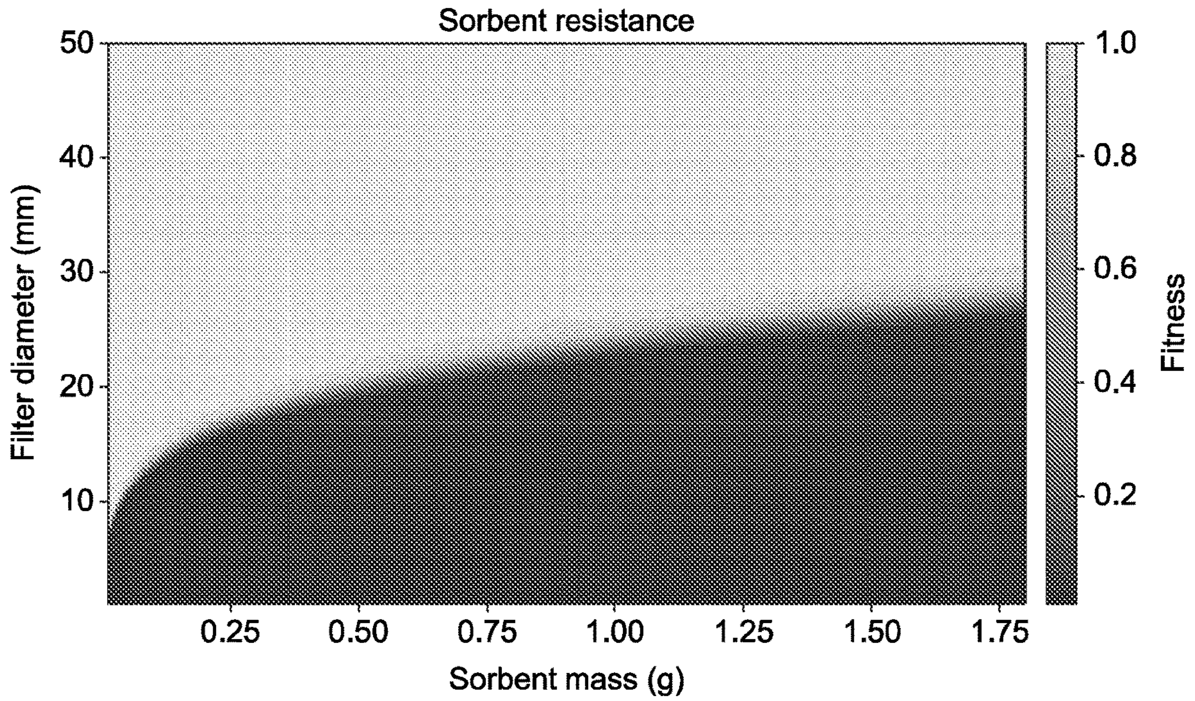

FIG. 8*g* plots the variation of the fitness value for an additional fitness value with respect to two parameters: filter (i.e. sorbent) diameter and sorbent mass. In this example, the fitness value is for sorbent resistance. FIG. 8*g* is one way to preferentially choose a low sorbent resistance. It is possible that some optimisations will give high sorbent resistance and low orifice resistance which is not as useful as a low sorbent resistance and high orifice resistance (because the orifice can be removed if it is found to be too restrictive to breath in clinical trials but the sorbent needs to be retained). It will be appreciated that the fitness value for sorbent resistance may also be incorporated into the method described above using iterative optimisation algorithms but is shown for the database only for simplicity.

Figure 9:
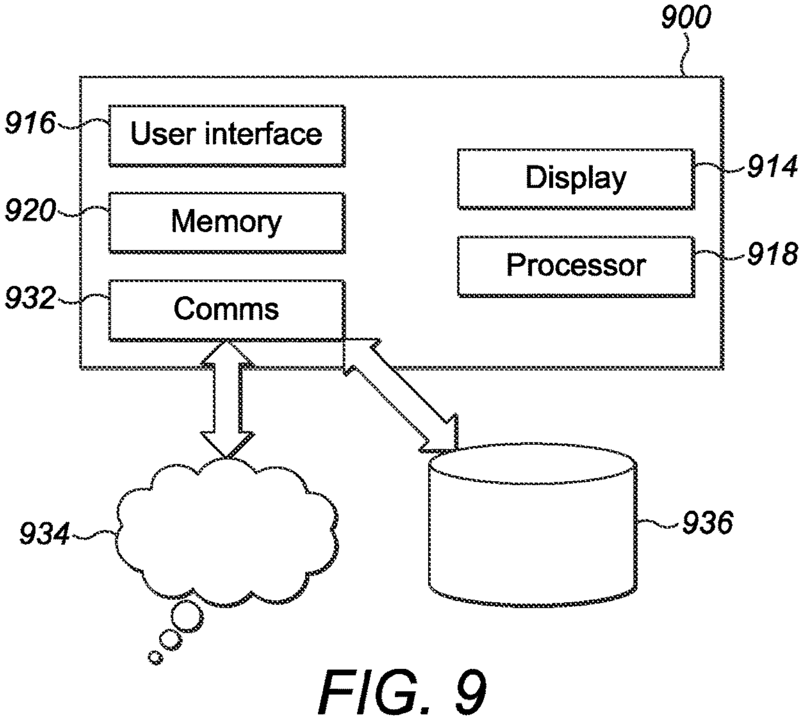
FIG. 9 is a schematic block diagram for a computing device which carries out the method of FIG. 5.

FIG. 9 shows a block diagram of the components of a computing device 900 for carrying out the method of FIG. 5. The computing device 900 may be any suitable device, e.g. a server, a personal computer or network of such devices. The functionality provided by the method above may be combined into fewer elements or separated into additional elements.

The computing device 900 comprises the standard components including, for example a display 914 (e.g. a screen) which displays information to a user (e.g. the output optimal values) and a user interface 916 through which a user can enter input (e.g. the nature of the sorbent material or any fixed parameters). The user interface may be any known user interface including a touch-sensitive screen, a keyboard or a voice activated interface. The computing device 900 comprises a processor 918 which processes instructions from apps running on the device. The processor may comprise one or more of: a microprocessor, a microcontroller, and an integrated circuit.

The computing device 900 also comprises memory 920 for storing information, such as the instructions for carrying out the method and some of the data which is saved in the method. The memory may comprise a volatile memory, such as random access memory (RAM), for use as temporary memory, and/or non-volatile memory such as Flash, read only memory (ROM), or electrically erasable programmable ROM (EEPROM), for storing data, programs, or instructions. The computing device 900 may also comprises a communication module 932 which allows the computing device 900 to connect to storage, e.g. to the cloud 934 or a database 936, to store data created during the method. Such storage may be remote, e.g. in a different location to the computing device 900.

Figure 10:
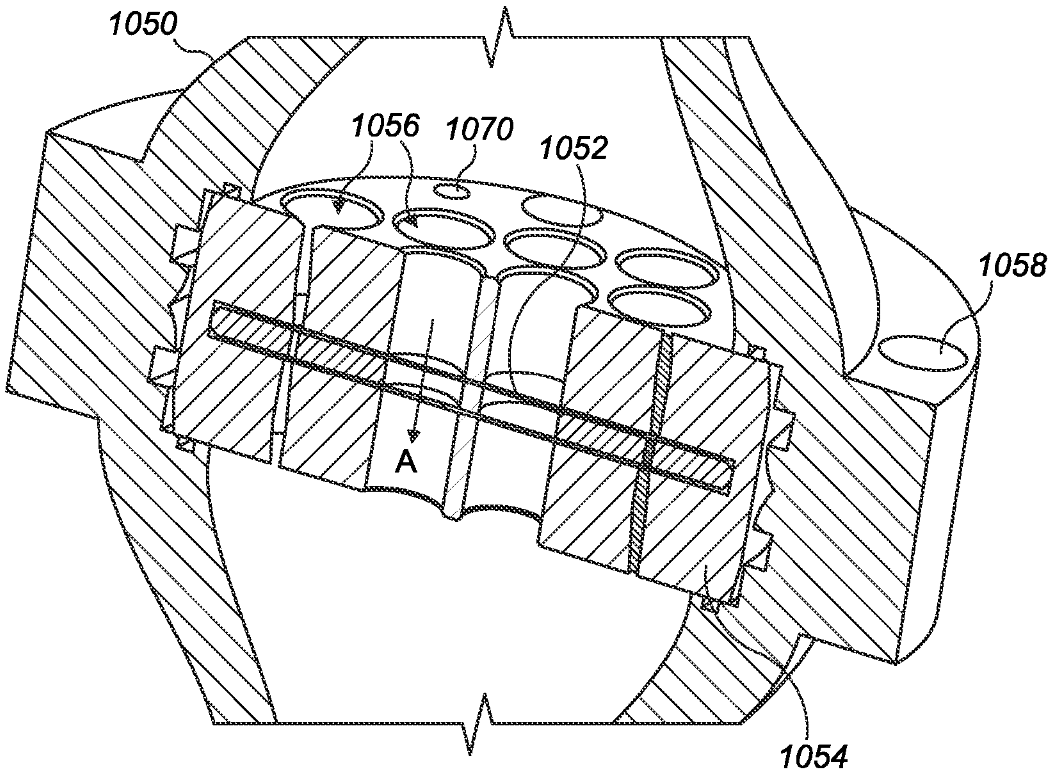
FIG. 10 is a partial cross-section showing an alternative arrangement.

The optimisation process above generated optimal values for the diameter of the sorbent material of 25.6 mm. Using variations of the fitness functions (e.g. with different values of a and b and/or only using one error function for the fitness function for airflow) and/or lung load lines shown above, it is possible to obtain different values for the diameter, e.g. 17.2 mm or 21.9 mm. As indicated by the fitness value, the optimal value of 25.6 mm is a little larger than desired. FIG. 10 shows a possible arrangement which addresses the issue of a large disk. In FIG. 10, a plurality of smaller disks having the same overall surface area as the single large disk are used. In this arrangement, there are twelve smaller disks of sorbent material 1052 which are supported in a sorbent holder 1054 within the sorbent housing 1050.

The sorbent holder 1054 comprises a plurality of channels 1056 (in this arrangement, 12) which define separate fluid paths through the sorbent holder 1054. The sorbent material 1052 is mounted centrally along the axis of each channel so that when a breath passes through the channel 1056 as indicated by arrow A, the breath passes through the sorbent material 1052. In this example, the channels 1056 are generally cylindrical but other designs may be used, e.g. tapering may be used when this prevents or alleviates movement of the sorbent material within the channel.

To facilitate construction, in this arrangement, the sorbent holder 1054 is formed in two pieces so that the sorbent material 1052 is sandwiched between the two parts. The two parts are held together by any suitable fixing mechanism 1070. The sorbent holder 1054 is made from any suitable material, e.g. from stainless steel when the sorbent material is baked at a high temperature before use. Similarly, the sorbent housing 1050 may be a two-part housing with the sorbent holder 1054 held in place between the two parts of the housing. The two parts of the housing are held together by any suitable fixing mechanism 1058.

The skilled person will appreciate that any other number of the holes may be used as long as the holes have the same equivalent total cross-sectional area as the optimized sorbent disk described below. For example, an arrangement in which the sorbent holder has three or five channels may be used.

Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others. All of the steps of any method or process so disclosed, may be combined in any combination, except combinations where at least some of such features and/or steps are mutually exclusive.

The contents of all such papers and documents referenced in this specification are incorporated herein by reference.

The invention claimed is:

1. A computer-implemented method of designing a breath sampling device comprising a housing which is configured to allow a substantial portion of an exhaled breath to pass through and sorbent material which extends across a cross-section of the housing, the method of designing the breath sampling device comprising:

identifying a plurality of parameters of the breath sampling device, wherein the plurality of parameters comprises at least two of mass of the sorbent material, size of the sorbent material, thickness of the sorbent material, resistance of the sorbent material, breakthrough volume and flowrate within the breath sampling device;

selecting a parameter value for each of the identified plurality of parameters of the breath sampling device by:

obtaining multiple parameter values for each of the identified plurality of parameters of the breath sampling device;

calculating fitness values for the obtained multiple parameter values, where each fitness value is calculated by:

defining a fitness function for each of the identified plurality of parameters of the breath sampling device, where the fitness function describes a variation in the fitness value between 0 and 1 as a function of the parameter value, where a fitness value of 0 is used for each parameter value that results in an unacceptable design for the breath sampling device and where a fitness value of 1 is used for each parameter value that results in an ideal design for the breath sampling device; and using the defined fitness function to calculate the fitness value for the obtained multiple parameter values;

combining the calculated fitness values for the obtained multiple parameter values for each of the identified plurality of parameters to obtain multiple global fitness values, where each global fitness value is a value which balances the fitness values for the obtained multiple parameter values for each of the identified plurality of parameters when designing the breath sampling device;

obtaining a maximum global fitness value and selecting the parameter value for each of the identified plurality of parameters of the breath sampling device based on the calculated fitness value for each of the identified plurality of parameters from the obtained maximum global fitness value; and outputting a design of the breath sampling device having the selected parameter value for each of the identified plurality of parameters.

2. The method of claim 1, where selecting a parameter value for each of the identified plurality of parameters of the breath sampling device comprises:

obtaining multiple parameter values for each of the identified plurality of parameters of the breath sampling device by setting initial values for each of the identified plurality of parameters;

calculating initial fitness values for each of the initial values for each of the identified plurality of parameters;

combining the initial fitness values to obtain an initial global fitness value; and running an optimisation algorithm which iteratively adjusts the initial values for each of the identified plurality of parameters and repeats the calculating and combining until the maximum global fitness value is obtained.

3. The method of claim 1, where selecting the parameter value for each of the identified plurality of parameters comprises indexing the multiple global fitness values to obtain the maximum global fitness value.

4. The method of claim 1, where combining the calculated fitness values for the obtained multiple parameter values for each of the identified plurality of parameters to obtain multiple global fitness values comprises determining a global fitness value of 0 when any one of the fitness values is 0.

5. The method of claim 1, where combining the calculated fitness values for the obtained multiple parameter values for each of the identified plurality of parameters to obtain multiple global fitness values comprises calculating at least one of the multiple global fitness values from a geometric mean of the combined fitness values.

6. The method of claim 1, where the fitness value for each of the breakthrough volume and the thickness of the sorbent material approaches 0 below a first threshold and 1 above a second threshold.

7. The method of claim 1, where the fitness value for each of the size of the sorbent material and the mass of the sorbent material approaches 1 below a first threshold and 0 above a second threshold.

8. The method of claim 1, where the fitness value for the flowrate within the breath sampling device approaches 0 below a first threshold and above a fourth threshold and approaches 1 above a second threshold and approaches 1 below a third threshold.

9. The method of claim 1, further comprising evaluating a specific value for the breakthrough volume and/or the flowrate before calculating the fitness value, where the specific value for the breakthrough volume and/or the flowrate are evaluated based on specific values for the mass, size and thickness of the sorbent material.

10. The method of claim 9, where the breath sampling device further comprises an orifice plate having an orifice with a diameter and the method of designing the breath sampling device comprises:

identifying orifice diameter as one of the identified plurality of parameters of the breath sampling device; and selecting a parameter value of the orifice diameter when selecting a parameter value for each of the identified plurality of parameters.

11. The method of claim 10, comprising selecting multiple parameter values of the orifice diameter, where each selected parameter value of the orifice diameter is for a different user.

12. The method of claim 10, further comprises evaluating a specific value of the flowrate based on a specific value of the orifice diameter.

13. A method of making a breath sampling device, the method comprising designing the breath sampling device as set out in claim 1, and making the breath sampling device to the output design of the breath sampling device having the selected parameter value for each of the identified plurality of parameters of the breath sampling device.

14. A non-transitory data carrier carrying code which, when implemented on a processor, causes the processor to carry out the method of claim 1.

15. The method of claim 1, where the fitness function is defined by at least one error function.

16. A breath sampling device comprising:

an inlet configured to receive exhaled breath in the device;

an outlet configured to allow exhaled breath to exit the device;

a housing connected between the inlet and the outlet and through which a substantial portion of the exhaled breath passes; and a sorbent material housed in the housing, where the sorbent material extends across a cross-section of the housing; and where the breath sampling device has been designed to have a selected parameter value for each of a plurality of parameters of the breath sampling device by:

identifying a plurality of parameters of the breath sampling device for which a parameter value is to be selected, where the plurality of parameters comprises at least two of mass of the sorbent material, size of the sorbent material, thickness of the sorbent material, resistance of the sorbent material, breakthrough volume and flowrate within the breath sampling device;

selecting the parameter value for each of the identified plurality of parameters of the breath sampling device by:

obtaining multiple parameter values for each of the identified plurality of parameters of the breath sampling device;

calculating fitness values for the obtained multiple parameter values, where each fitness value is calculated by:

defining a fitness function for each of the identified plurality of parameters of the breath sampling device, where the fitness function describes a variation in the fitness value between 0 and 1 as a function of the parameter value, where a fitness value of 0 is used for each parameter value that results in an unacceptable design for the breath sampling device and where a fitness value of 1 is used for each parameter value that results in an ideal design for the breath sampling device; and using the defined fitness function to calculate the fitness value for the obtained multiple parameter values;

combining the calculated fitness values for the obtained multiple parameter values for each of the identified plurality of parameters to obtain multiple global fitness values, where each global fitness value is a value which balances the fitness values for the obtained multiple parameter values for each of the identified plurality of parameters when designing the breath sampling device;

obtaining a maximum global fitness value and selecting the parameter value for each of the identified plurality of parameters of the breath sampling device based on the calculated fitness value for each of the identified plurality of parameters from the obtained maximum global fitness value.

17. The breath sampling device of claim 16, where the sorbent material has a thickness of approximately 4.03 mm and a cross-sectional area of approximately 232 $mm^2$ or the sorbent material has a thickness of approximately 2.5 mm and a cross-sectional area of approximately 376 $mm^2$ or the sorbent material has a thickness of approximately 3.12 mm and a cross-sectional area of approximately 515 $mm^2$.

18. The breath sampling device of claim 16, where the sorbent material comprises a plurality of discrete portions of sorbent material supported in a sorbent holder.

19. The breath sampling device of claim 16, further comprising an indicator indicating a volume of total breath which has been sampled by the device.

20. The breath sampling device of claim 16, further comprising an orifice plate between the sorbent material and the outlet.

21. The breath sampling device of claim 16, further comprising a bypass component which is configured to allow an initial portion of an exhaled breath to exit the device without being sampled by the sorbent material.

* * * * *